(12) United States Patent
Brachman et al.

(10) Patent No.: US 10,085,699 B2
(45) Date of Patent: *Oct. 2, 2018

(54) RADIATION SHIELDING

(71) Applicant: GT MEDICAL TECHNOLOGIES, INC., Mesa, AZ (US)

(72) Inventors: David Brachman, Gilbert, AZ (US); Evan K. Fram, Phoenix, AZ (US); Peter Nakaji, Phoenix, AZ (US)

(73) Assignee: GT Medical Technologies, Inc., Mesa, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/377,014

(22) Filed: Dec. 13, 2016

(65) Prior Publication Data
US 2017/0215824 A1    Aug. 3, 2017

Related U.S. Application Data

(63) Continuation of application No. 15/147,826, filed on May 5, 2016, now Pat. No. 9,526,463.

(60) Provisional application No. 62/157,871, filed on May 6, 2015.

(51) Int. Cl.
G21F 1/00 (2006.01)
A61B 6/10 (2006.01)
G21F 1/02 (2006.01)
A61N 5/10 (2006.01)

(52) U.S. Cl.
CPC .............. *A61B 6/107* (2013.01); *G21F 1/02* (2013.01); *A61N 5/1001* (2013.01); *A61N 2005/1094* (2013.01)

(58) Field of Classification Search
CPC ......... A61B 6/107; G21F 1/02; A61N 5/1001; A61N 2005/1094
USPC ................... 250/505.1, 515.1, 506.1, 507.1
See application file for complete search history.

(56) References Cited

U.S. PATENT DOCUMENTS

| D244,393 S | 5/1977 | Collica et al. |
| 4,706,652 A | 11/1987 | Horowitz |
| 4,754,745 A | 7/1988 | Horowitz |
| 4,946,435 A | 8/1990 | Suthanthiran et al. |
| 5,030,195 A | 7/1991 | Nardi |
| D381,080 S | 7/1997 | Ohata |
| 5,772,574 A | 6/1998 | Nanko |
| 5,803,895 A | 9/1998 | Kronholz et al. |
| 5,840,008 A | 11/1998 | Klein et al. |

(Continued)

FOREIGN PATENT DOCUMENTS

| DE | 613 528 | 5/1935 |
| EP | 0 292 630 B1 | 8/1995 |

(Continued)

OTHER PUBLICATIONS

Search and Examination Report; Application No. P1140/13; Filed on Oct. 24, 2013 (PCT dated Apr. 30, 2012); 10 pages.

(Continued)

*Primary Examiner* — Nicole Ippolito
*Assistant Examiner* — Hanway Chang
(74) *Attorney, Agent, or Firm* — Knobbe, Martens, Olson & Bear LLP

(57) ABSTRACT

Various configurations of shielding materials within shielding layers, such as for use in shielding radiation from implanted radioactive carriers, are discussed herein.

22 Claims, 16 Drawing Sheets

(56) References Cited

U.S. PATENT DOCUMENTS

| | | |
|---|---|---|
| 5,871,708 A | 2/1999 | Park et al. |
| D408,957 S | 4/1999 | Sandor |
| 5,967,966 A | 10/1999 | Kronholz et al. |
| 5,997,842 A | 12/1999 | Chen |
| 6,017,482 A | 1/2000 | Anders et al. |
| D420,452 S | 2/2000 | Cardy |
| D420,745 S | 2/2000 | Cardy |
| D420,746 S | 2/2000 | Cardy |
| 6,129,670 A | 10/2000 | Burdette et al. |
| D443,061 S | 5/2001 | Bergstrom et al. |
| 6,248,057 B1 | 6/2001 | Mavity et al. |
| 6,327,490 B1 | 12/2001 | Spetz |
| 6,358,195 B1 | 3/2002 | Green et al. |
| 6,360,116 B1 | 3/2002 | Jackson et al. |
| 6,385,477 B1 | 5/2002 | Werner et al. |
| 6,450,937 B1 | 9/2002 | Mercereau et al. |
| 6,471,631 B1 | 10/2002 | Slater et al. |
| 6,512,943 B1 | 1/2003 | Kelcz |
| 6,712,508 B2 | 3/2004 | Nilsson et al. |
| D488,864 S | 4/2004 | Fago et al. |
| 6,787,042 B2 | 9/2004 | Bond et al. |
| 7,011,619 B1 | 3/2006 | Lewis |
| D561,896 S | 2/2008 | Jones |
| D580,056 S | 11/2008 | Orthner |
| D580,057 S | 11/2008 | Ramadani |
| 7,776,310 B2 | 8/2010 | Kaplan |
| 8,039,790 B2 | 10/2011 | Cho et al. |
| D657,474 S | 4/2012 | Dona |
| D680,649 S | 4/2013 | Jagger et al. |
| D681,210 S | 4/2013 | Beiriger et al. |
| D681,812 S | 5/2013 | Farris et al. |
| D681,813 S | 5/2013 | Jagger et al. |
| D686,341 S | 7/2013 | Nakaji et al. |
| D686,744 S | 7/2013 | Nakaji et al. |
| D686,745 S | 7/2013 | Nakaji et al. |
| D686,746 S | 7/2013 | Nakaji et al. |
| D686,747 S | 7/2013 | Nakaji et al. |
| D686,748 S | 7/2013 | Nakaji et al. |
| D687,568 S | 8/2013 | Nakaji et al. |
| D687,966 S | 8/2013 | Nakaji et al. |
| D687,967 S | 8/2013 | Nakaji et al. |
| 8,600,130 B2 | 12/2013 | Eriksson Järliden |
| 8,605,966 B2 | 12/2013 | Erisson Järliden |
| 8,825,136 B2 | 9/2014 | Giller et al. |
| 8,876,684 B1 | 11/2014 | Nakaji et al. |
| 8,939,881 B2 | 1/2015 | Nakaji et al. |
| 8,974,364 B1 | 3/2015 | Nakaji et al. |
| 9,022,915 B2 | 5/2015 | Nakaji et al. |
| 9,403,033 B1 | 8/2016 | Brachman |
| 9,409,038 B2 | 8/2016 | Nakaji et al. |
| 9,492,683 B2 | 11/2016 | Brachman et al. |
| 9,526,463 B2 * | 12/2016 | Brachman .............. A61B 6/107 |
| 9,545,525 B2 | 1/2017 | Nakaji et al. |
| 2001/0044567 A1 | 11/2001 | Zamora et al. |
| 2002/0058854 A1 | 5/2002 | Creed et al. |
| 2003/0045769 A1 | 3/2003 | Kalas et al. |
| 2003/0088141 A1 | 5/2003 | Terwilliger et al. |
| 2003/0130573 A1 | 7/2003 | Yu et al. |
| 2003/0208096 A1 | 11/2003 | Tam |
| 2004/0109823 A1 | 6/2004 | Kaplan |
| 2004/0116767 A1 | 6/2004 | Lebovic et al. |
| 2004/0242953 A1 | 12/2004 | Good |
| 2005/0035310 A1 | 2/2005 | Drobnik et al. |
| 2005/0244045 A1 | 11/2005 | Eriksson |
| 2006/0015030 A1 | 1/2006 | Poulin et al. |
| 2006/0063962 A1 | 3/2006 | Drobnik et al. |
| 2006/0173236 A1 | 8/2006 | White et al. |
| 2006/0235365 A1 | 10/2006 | Terwilliger |
| 2007/0225544 A1 | 9/2007 | Vance et al. |
| 2008/0004714 A1 | 1/2008 | Lieberman |
| 2008/0146861 A1 | 6/2008 | Murphy et al. |
| 2008/0221384 A1 | 9/2008 | Chi Sing et al. |
| 2009/0012347 A1 | 1/2009 | Helle |
| 2009/0131735 A1 | 5/2009 | Drobnik et al. |
| 2009/0253950 A1 | 10/2009 | Rapach et al. |
| 2009/0271715 A1 | 10/2009 | Tumuluri |
| 2010/0056908 A1 | 3/2010 | Giller et al. |
| 2010/0200778 A1 | 8/2010 | Drobnik et al. |
| 2010/0228074 A1 | 9/2010 | Drobnik et al. |
| 2010/0268015 A1 | 10/2010 | Drobnik et al. |
| 2010/0288916 A1 | 11/2010 | Cho et al. |
| 2010/0324353 A1 | 12/2010 | Helle |
| 2011/0013818 A1 | 1/2011 | Eriksson Järliden |
| 2011/0206252 A1 | 8/2011 | Eriksson Järliden |
| 2013/0131434 A1 | 5/2013 | Nakaji et al. |
| 2013/0338423 A1 | 12/2013 | Nakaji et al. |
| 2014/0275715 A1 | 9/2014 | Brachmann et al. |
| 2014/0316187 A1 | 10/2014 | Nakaji et al. |
| 2015/0057487 A1 | 2/2015 | Nakaji et al. |
| 2015/0140535 A1 | 5/2015 | Geri et al. |
| 2015/0196778 A1 | 7/2015 | Nakaji et al. |
| 2015/0321024 A1 | 11/2015 | Nakaji et al. |
| 2015/0367144 A1 | 12/2015 | Flynn et al. |
| 2017/0021191 A1 | 1/2017 | Brachman et al. |
| 2017/0120073 A1 | 5/2017 | Brachman et al. |
| 2017/0252575 A1 | 9/2017 | Nakaji et al. |

FOREIGN PATENT DOCUMENTS

| | | |
|---|---|---|
| EP | 0 906 769 A2 | 4/1999 |
| JP | S52-9424 | 7/1975 |
| JP | H09-028810 | 4/1997 |
| JP | 2001-266903 | 9/2001 |
| JP | 3095304 | 7/2003 |
| JP | 2007-512112 | 5/2007 |
| JP | 2009-515603 | 4/2009 |
| JP | 2010-536529 | 12/2010 |
| WO | WO 2007/106531 A1 | 9/2007 |
| WO | WO 2012/100206 A2 | 7/2012 |
| WO | WO 2012/149580 A1 | 11/2012 |
| WO | WO 2016/171961 | 10/2016 |
| WO | WO 2016/179420 | 11/2016 |

OTHER PUBLICATIONS

Cole, P.D., et al., "A comparative long-term assessment of four soft tissue supplements". Anesthetic Surg J. 31(6). 674-681, 2011.

International Search Report; International Application No. PCT/US2012/035907, dated Sep. 26, 2012; 3 pages.

International Search Report; International Application No. PCT/US2012/035909, dated Aug. 30, 2012; 3 pages.

Crepeau, R.H., et al., "Image Processing of Imperfect Protein Arrays: Sectioned Crystals and Tubulin Sheets and Rings". Elec. Microsc. Soc. Amer. Proc. 40:84-87, 1982.

Crepeau, R.H., et al., "Reconstruction of imperfectly ordered zinc-induced tubulin sheets using cross-correlation and real space averaging". Ultramicroscopy, 6, 7-18, 1981.

Dagnew, E., et al., "Management of newly diagnosed single brain metastasis using resection and permanent iodine-125 seeds without initial whole-brain radiotherapy: a two institution experience". Neurosurg Focus. 15; 22(3):E3, 2007.

Delaney, T.F., et al., "Intraoperative dural irradiation by customized 1921 iridium and 90 Yttrium brachytherapy plaques". Int. J. Radiat Oncol Biol Phys. 57(1): 239-245, 2003.

Gutin, P.H., et al., "A coaxial catheter system for afterloading radioactive sources for the interstitial irradiation of brain tumors. Technical note". J. Neurosurg 56: 734-735, 1982.

Gutin, P.H., et al., "Brachytherapy of recurrent tumors of the skull base and spine with iodine-125 sources". Neurosurgery 20:938-945, 1987.

Hamilton, A.J., et al., "The use of gold foil wrapping for radiation protection of the spinal cord for recurrent tumor therapy". Int. J. Radiat Oncol Biol Phys. 32(2):507-511, 1995.

Hilaris, B.S., et al., "Interstitial irradiation for unresectable carcinoma of the lung". Ann Thoracic Surg; 20:491-500, 1975.

Hilaris, B.S., et al., "Intraoperative radiotherapy in stage I and II lung cancer". Semin Surg Oncol. 3:22-32, 1987.

Huang, K., et al., "Surgical resection and permanent iodine-125 brachytherapy for brain metastases". J. Neurooncol. 91:83-93, 2009.

(56) References Cited

OTHER PUBLICATIONS

Jenkins, H.P., et al., "Clinical and experimental observations on the use of a gelatin sponge or foam". Surg 20:124-132, 1946.
Kneschaurek, P. et al.: "Die Flabmethode Zur Intraoperativen Bestrahlung. Öthe Flab-Method for Intraoperative Radiation Therapy", Strahlentherapie and Oknologie, Urban Und Vogel, Muenchen, DE, vol. 171, No. 2; Feb. 1, 1995, pp. 61-69, XP000610565, ISSN:0179-7158.
Marchese, M.J., et al., "A versatile permanent planar implant technique utilizing iodine-125 seeds imbedded in gelfoam". Int J Radiat Oncol Biol Phys 10:747-751, 1984.
Murphy, M.K., et al., "Evaluation of the new cesium-131 seed for use in low-energy x-ray brachytherapy". Med Phy 31(6): 1529-1538, Jun. 2004.
Nori, D., et al., "Intraoperative brachytherapy using Gelfoam radioactive plaque implants for resected stage III non-small-cell lung cancer with positive margin: A pilot study". J Surg Oncol. 60:257-261, 1995.
Parashar, B., et al., "Cesium-131 permanent seed brachytherapy: Dosimetric evaluation and radiation exposure to surgeons, radiation oncologists, and staff". Brachytherapy. 10:508-511, 2011.
Patel, S., et al., "Permanent iodine-125 interstitial implants for the treatment of recurrent Glioblastoma Multiforme". Neurosurgery 46 (5) 1123-1128, 2000.
Rivard, M.J., "Brachytherapy dosimetry parameters calculated for a 131 Cs source". Med Phys. 34(2): 754-765, 2007.
Rogers, C.L., et al., "Surgery and permanent 125-1 seed paraspinal brachytherapy for malignant tumors with spinal cord compression". Int. J. Radial Oncol Biol Phys. 54(2): 505-513, 2002.
Wernicke, A.G., et al., "Feasibility and safety of Gliasite brachytherapy in the treatment of CNS tumors following neurosurgical resection". J. Cancer Res Ther. 6(1), 65-74, Jan.-Mar. 2010.
Office Action dated Apr. 2, 2015; European Patent Application No. 12724426.7; 5 pages.
Office Action dated Oct. 30, 2015; European Patent Application No. 12724426.7; 4 pages.
Office Action dated Feb. 9, 2016; Japanese Application No. 2014-508190; 5 pages including english translation.
International Search Report; International Application No. PCT/US2016/031035; filed May 5, 2016; 15 pages.
International Search Report and Written Opinion; International Application No. PCT/US2016/027143, filed Apr. 12, 2016; dated Aug. 25, 2016; 7 pages.
Decision of Rejection dated Feb. 4, 2016, Japanese Patent Application No. 2014-508190 with English Translation; 4 pages.
Ewersten, et al., "Biopsy Guided by Real-Time Sonography Fused with MRI: A Phantom Study", American Journal of Roentgenology. 2008; 190: 1672-1674. 10.2214/AJR.07.2587.
Summons to Attend Oral Proceedings dated Aug. 18, 2017; European Application No. 12724426.7; 5 pages.

* cited by examiner 1-5 cm
1-5 cm 8-25 mm diameter

Trim lines (e.g., 1cm x 1 cm grids)

5cm
5cm

Cut to custom size/shape 0.05 – 1 mm | SHIELDING LAYER 0.05 – 2.0 mm | COLLAGEN
0.05 – 2.0 mm | SHIELDING LAYER 0.05 – 2.0 mm | SHIELDING LAYER
0.05 – 2.0 mm | COLLAGEN 0.05 - 1.0 mm | COLLAGEN
0.05 - 1.0 mm | SHIELDING LAYER
0.05 - 1.0 mm | SHIELDING LAYER
0.05 - 1.0 mm | COLLAGEN 0.4 – 2.0 mm | COLLAGEN — 492
0.05 - 1.0 mm | SHIELDING LAYER — 494
0.05 - 1.0 mm | SHIELDING LAYER — 496
1.0 - 10mm | COLLAGEN — 498

Rod or Wires

702

Cylinder

704

Bar

706

RADIATION SHIELDING

CROSS-REFERENCE TO RELATED APPLICATIONS

This application a continuation of U.S. application Ser. No. 15/147,826, filed on May 5, 2016, which is a non-provisional of and claims the benefit of U.S. Provisional Application No. 62/157,871, filed on May 6, 2015, the entirety of which is hereby incorporated herein by reference.

FIELD

The inventions discussed herein generally relate to devices used in conjunction with radiation therapy.

BACKGROUND

Tumors in living organisms are highly variable in size, location and their amount of infiltration into normal tissues, the variability of tumors in general make them very difficult to treat with a one-size fits all approach. Furthermore, the extent of tumors and/or void upon debulking are typically not known until presented in the operating room. Thus the options necessary to effectively treat a tumor or tumor bed need to be quite diverse.

Brachytherapy involves placing a radiation source either into or immediately adjacent to a tumor. It provides an effective treatment of cancers of many body sites. Brachytherapy, as a component of multimodality cancer care, provides cost-effective treatment. Brachytherapy may be intracavitary, such as when treating gynecologic malignancies; intraluminal, such as when treating esophageal or lung cancers; external surface, such as when treating cancers of the skin, or interstitial, such as when treating various central nervous system tumors as well as extracranial tumors of the head and neck, lung, soft tissue, gynecologic sites, rectum, liver, prostate, penis and skin.

BRIEF DESCRIPTION OF THE DRAWINGS

The principles of the present invention will be apparent with reference to the following drawings, in which like reference numerals denote like components.

DETAILED DESCRIPTION

Figure 1A:
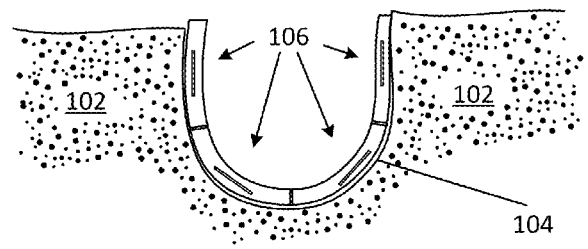
FIGS. 1A, 1B, and 1C are cross-sectional drawings illustrating a portion of patient tissue having radioactive carriers placed thereon.

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Overview

Tumors are difficult to eradicate surgically as their infiltrative nature often precludes microscopically complete resection without undue morbidity or mortality. This local persistence of tumor cells may be controlled if sufficient radiation can be delivered safely prior to regrowth and replication of the residual tumor cells. Debulking surgery, followed by radiation therapy may be used for local control of a tumor. Discussed herein are various systems, methods, and devices for use in conjunction with radiation therapy, such as to deliver (and to control delivery of) radiation to a post-operative tumor bed.

Definitions

In order to facilitate an understanding of the systems and methods discussed herein, a number of terms are defined below. The terms defined below, as well as other terms used herein, should be construed to include the provided definitions, the ordinary and customary meaning of the terms, and/or any other implied meaning for the respective terms. Thus, the definitions below do not limit the meaning of these terms, but only provide exemplary definitions.

Tumor: an abnormal growth of tissue resulting from uncontrolled, progressive multiplication of cells. Tumors can be benign or malignant.

Tumor bed: an anatomical area of a patient (e.g., a human or other mammal) where a tumor exists (pre-operative tumor bed) and/or an area surrounding a surgically removed tumor (post-operative tumor bed), such as a cranial cavity from which a tumor was surgically removed. Even after surgical removal of a tumor, the remaining tumor bed of the patient may include tumor cells.

Treatment area: an anatomical area that is targeted for delivery of radiation, such as from one or more radiation delivery devices (e.g., the carriers discussed below). A treatment area may include tissue below and/or around a location where the radiation deliver device is positioned, such as an anatomical area of a tumor or a tumor bed.

Treatment surface: an anatomical surface of a patient where a radiation delivery device is to be placed to deliver radiation to a treatment area, such as the treatment surface itself and/or tissue below the treatment surface. A treatment surface may be a portion of a tumor bed or any other anatomical surface. For example, if a tumor bed is surgically created, the treatment surface may include an entire exposed surface of the tumor bed, a portion of such exposed surface, or the entire exposed surface of the tumor bed as well as a surrounding area of tissue.

Brachytherapy: radiation treatment in which the radiation delivery device is placed directly on and/or close to a treatment surface of the body, such as directly on the surface of the body, within the body, or in a tumor bed. For example, brachytherapy may be intracavitary, such as in cranial or gynecologic malignancies; intraluminal, such as in esophageal or lung cancers; external, such as in cancers of the skin; and/or interstitial, such as in treatment of various central nervous system tumors as well as extracranial tumors of the head, neck, lung, soft tissue, gynecologic sites, rectum, liver, prostate, and penis.

Seed: a radioactive material that is configured for delivery of radiation to a tumor and/or tumor bed. A seed may be in various shapes and sizes, such as cylinder, cone, sphere, pyramid, cube, prism, rectangular prism, triangular prism, and/or any combination of these or other shapes. While seeds are generally referred to herein as cylindrical, any other shape or size of seed may alternatively be used in the various systems and methods discussed herein. Seeds may comprise any combination of one or more of multiple radioactive components, such as Cs 131, Ir 192, I 125, Pd 103, for example. Seeds may include a protective outer shell that partially or fully encases the radioactive material. Seeds are one form of radiation source. The term "radiation source," as used herein, generally refers to a radioactive seed (or other object that emits radiation), either alone (e.g., a seed) or embedded, or otherwise attached to, a carrier (e.g., a tile carrier with an embedded radioactive seed).

Carrier: a substrate that holds or contains a radioactive seed. A carrier that contains one or more seeds is a radiation delivery device. Carriers may be configured for permanent implantation into a tumor bed, such as to provide radioactive energy to a treatment surface surrounding an area where a tumor has been removed in order to treat any remaining malignant tissue. Carriers can be composed of various materials and take on various shapes and sizes. Examples carriers, such as carriers having various sizes, shapes, configurations, etc., are included in the following patent and patent application, each of which is hereby incorporated by reference in its entirety and for all purposes:

U.S. patent application Ser. No. 14/322,785, filed Jul. 2, 2014, now U.S. Pat. No. 8,876,684, entitled "Dosimetrically Customizable Brachytherapy Carriers and Methods Thereof In The Treatment Of Tumors," and U.S. patent application Ser. No. 14/216,723, filed Mar. 17, 2014, publication No. 2014/0275715, entitled "Dosimetrically Customizable Brachytherapy Carriers and Methods Thereof In The Treatment Of Tumors."

Tile Carrier (also referred to as "Tile"): type of carrier that is substantially planar and generally maintains a two-dimensional planar geometry when placed in a tumor bed. Depending on the material of the tile, though, the tile may be malleable such that the tile can be deformed by bending in order to better conform to a tumor bed. For example, for tiles consisting essentially of collagen (and/or other malleable materials), the tiles may be substantially bent as placed in or on a treatment surface (and/or when pressed against the treatment surface) to conform with the shape of the treatment surface, such as a post-operative tumor bed.

Gore Carrier (also referred to as "Gore"): type of carrier that is 3-dimensional and conforms to the tumor bed while maintaining the geometry necessary for an effective implant. In some embodiments, gores are initially planar and are reconfigured to take on a 3-dimensional shape, such as to form a hemispherical surface that may be placed into a similarly shaped tumor cavity.

Loader: a device that aids in placement of radioactive seeds in carriers, such as via injection of seeds into carriers. A loader, also referred to herein as a "loading device," may include multiple components, such as to hold a carrier in place and guide a delivery device (e.g., a needle or injector) into the carrier in order to place a seed at a precise location in the carrier. U.S. patent application Ser. No. 13/460,809, filed Apr. 30, 2012, now U.S. Pat. No. 8,939,881, entitled "Apparatus For Loading Dosimetrically Customizable Brachytherapy Carriers," and U.S. patent application Ser. No. 14/696,293, filed Apr. 24, 205, entitled "Apparatus and Method for Loading Radioactive Seeds Into Carriers," which are each hereby incorporated by reference in their entirety for all purposes, describe several embodiments of loaders. As discussed further herein, loaders may be operated manually, such as by human operators, or may be fully automated, such that carriers can be loaded with seeds using an automated process. Alternatively, loaders may be configured to be automated in part and require manual operation in part.

High Z Materials: any element with an atomic number greater than 20, or an alloy containing such materials.

Shielding Specifications (also referred to as a "Shielding plan"): attributes of one or more isolation sheets, such as attributes of shielding layers and any other layers (e.g., collagen or other spacing layer, adhesive layers, etc.) included in the isolation sheets, such as any combination of those attributes (also referred to herein as "characteristics") of shielding material(s)s, shielding layer(s), and/or isolation sheet(s) that are discussed below. Shielding specifications may be in digital form (e.g., in an electronic data structure, such as a database or table), written form (handwritten by an oncologist or surgeon or printed from a digital form), and/or may be developed and/or updated without (or prior to) placement of the isolation sheet(s). Thus, shielding specifications may be developed in real-time based on clinical need and/or other patient characteristics.

Shielding specifications may be determined to best meet one or more of many clinical needs (and/or other shielding goals or requirements), such as to provide one or more isolation sheets that:

shield radiation from one or radiation sources to result in a directional therapeutic treatment area. Radiation sources, such as carriers embedded with radioactive seeds, generally emit radiation in an omnidirectional manner, such that all areas around the radiation sources absorb radiation (possibly in varying amounts depending on the shape, size, placement, etc. of the radiation source). Shielding specifications may be set to reduce the range of radiation by blocking radiation emit in certain directions;

reduce risk of imaging distortion due to interference by the shielding materials (or other components) of the isolation sheets;

reduce risk of RF heating caused by energy from MRI or other imaging devices, thereby reducing risk of further patient injuries, such as burning, as a result of imaging;

provide a preferred (or required in some embodiments) malleability of the isolation sheets, such as to allow placement of the isolation sheets in irregularly shaped treatment areas; and/or reduce risk of deflection (e.g., movement) of the isolation sheets (and/or individual shielding materials within the isolation sheets) by energy from imaging devices, such as MRI.

Several of the potential risks and/or limitations noted above, as well as others, associated with use of MRI with shielding materials (such as in an isolation sheet), as well as other implants and devices, are discussed in "MRI Bioeffects, Safety, and Patient Management," Chapter 16, by Frank G. Shellock, Ph.D. and John V. Crues, III, M.D., *Biomedical Research Publishing Group*, 7751 Veragua Drive, Playa Del Rey, Calif. 90293, accessed Oct. 16, 2013, which is hereby incorporated by reference for all purposes, including its teachings regarding potential risks and/or limitations associated with use of MRI with medical implants and devices. In some embodiments, shielding specifications for isolation sheets may be determined or modified based on other potential risks or limitations described in this book.

Shielding Material: any material that restricts movement of radioactive particles, such as by absorbing, reflecting, and/or scattering radioactive particles. The term "shielding," as used herein, generally refers to any mechanism of preventing radiation from moving through and exiting a corresponding shielding material, such as by the shielding material absorbing, reflecting, or otherwise blocking the radiation. Shielding materials in various forms may be used in the various embodiments discussed herein. For example, a shielding material may be in the form of a particle, wire, rod, cylinder, bar, sheet, liquid, solution, foam, or any other form in which a material having radiation absorbing and/or reflecting properties is possible. A shielding material provides a shielding rate, which is generally an amount of shielding of radioactive energy (that is emitted from one or more radiation sources), provided by the particular shielding materials. Similarly, a shielding layer comprising multiple shielding materials and an isolation sheet have associated shielding rates, which are dependent on the combination of shielding (and possibly non-shielding) materials therein. For some applications, such as based on clinical need, an isolation sheet that provides a shielding rate of 25%, 50%, 75%, 90%, 95%, 98%, or some other shielding percentage, may be desired. As discussed herein, material composition, shape, size, dimensions, etc. may impact the shielding abilities of a shielding material. For applications (e.g., based on clinical need) where a higher shielding percentage is desired than may be provided by a single shielding material, multiple shielding materials may be used in combination, in one or more shielding layers or isolation sheets.

In some embodiments, shielding materials comprise high Z materials, such as tantalum, gold, platinum, tin, steel, copper, aluminum, etc. (e.g., a 0.05 mm to 0.2 mm thickness metallic foil). In other embodiments, any other material that reduces penetration of radiation may be a shielding material. For example, a non-metallic, yet dense compound, may be used alone (or in combination with a metallic material) as a shielding material. Such a non-metallic shielding material may advantageously lessen the chance of 1) MRI artifacts, 2) deflection of the isolation sheet, and/or 3) MRI-induced heating, such as may be caused by current loop induction and/or radio-frequency induced tissue heating that may be caused by metallic shielding materials. Depending on the particular non-metallic material, thickness of the material may be larger than a required thickness of a metallic shielding material, in view of the general enhanced shielding abilities of metallic materials. Non-metallic high density shielding materials may beneficially provide shielding of non-target tissues from radiation particularly in applications where MRI or other magnetic field exposure may be anticipated. Examples of non-metallic shielding materials include polyetheretherketone (PEEK), nanoparticles, polymeric nanoparticles, encapsulated nanoparticles, calcium carbonate, calcium phosphate, calcium sulfate, barium sulfate, zirconium dioxide, polymers and polymer hybrids of these and other materials. Shielding materials may be combined to form a composite shielding material. For example, a metallic cylinder may be filled with (non-metallic) liquid calcium carbonate, in order to form a shielding material that better addresses one or more of the clinical needs of the patient than a separate metallic cylinder and liquid calcium carbonate or a solid metallic rod.

Any reference herein to a shielding material, even if the example references a particular metallic or non-metallic material (e.g., a particular form of a particular material), could be implemented with any other shielding material (e.g., a different form and/or different material) and/or combination of shielding materials. For example, a golden rod shielding material be replaced with a PEEK mesh shielding material that provides similar radiation absorption and/or reflecting properties. Dimensions (e.g., width, height, radius, thickness, etc.) of various shielding materials that provide the same radiation absorption and/or reflective properties may vary from one material to another.

Shielding Layer: one or more shielding materials configured for placement on or near radioactive sources (e.g., seeds) for reducing penetration of radiation outside of a treatment area. A shielding layer may comprise discrete layers of one or more materials, such as a gold foil sheet or a polymer sheet. In other embodiments, a shielding layer may include particles of high Z or non-metallic material that may be embedded within a shielding layer substrate (comprising a shielding layer material), such as collagen or other bio-compatible material. For example, a collagen shielding layer substrate may be embedded with one or more shielding materials arranged in a configuration that provides shielding for a particular patient (e.g., based on a planned use of radioactive carriers in treating the patient). For example, a shielding layer may include one or more rods, braids, hollow rods, tubules (or tubes), bars, dots (or spheres), trapezoids, or other shape, shielding materials embedded in a shielding layer substrate, or adhered to one another without use of a shielding layer substrate.

Isolation Sheet: A single shielding layer or combination of multiple shielding layers, such as adhered to one another in a predetermined configuration in order to provide desired radiation shielding, while limiting imaging artifacts. In some embodiments, isolation sheets may include multiple shielding layers in a grid or mesh pattern, either alone or filled with, encapsulated by, or a combination of filled and encapsulated with, shielding materials, in various configurations and/or patterns. The pattern of shielding materials in the one or more shielding layers advantageously improves effectiveness of the isolation sheet in shielding radioactive energy, as well as ease of handling (e.g., malleability that allows placement in the treatment area in the desired configuration) and/or imaging characteristics (e.g., reduces artifacts from shielding materials).

For some isolation sheets, the closer they are placed to the radiation source, the more protection the one or more shielding layers of the isolation sheet will have, given the geometric dispersal pattern of the radiation. Additionally, thicker isolation sheets can provide more effective blocking of the transmitted energy. However, especially with metallic shielding materials, thicker shielding layers (and corresponding isolation sheets comprising such thicker shielding layers) may cause undesirable effects such as artifact, radiofrequency heating, or other issues. In addition, thicker isolation sheets may have undesirable handling characteristics, including stiffness and bulk. Thus, in some embodiments, shielding layers may include smaller, thinner, segmented, braided, and/or discontinuous shielding materials that provide greater pliability and help alleviate these concerns, especially when multiple shielding layers are used in an isolation sheet. Many variations of shielding layers and isolation sheets are discussed herein, but there are many other combinations of shielding materials, patterns of placement of shielding materials within a shielding layers, quantities and/or relative alignment of multiple shielding layers within an isolation sheet, etc. that are possible based on this disclosure. To the extent shielding materials provide shielding through scattering or reflection of radiation, multiple shielding layers and/or multiple layers of shielding materials within a single shielding layer may provide a higher shielding rate, such as by subsequent layers absorbing (or otherwise shielding) radiation remaining (e.g., scattered) from the previous layer, eventually reducing the energy to a suitable level.

Dosimetry: a process of measurement and quantitative description of the radiation absorbed dose (e.g., rad) in a tissue or organ.

Dosimetric Plan: a description of the prescribed dosimetry, such as for a particular patient, associated with a particular clinical condition, and/or for use in a particular surgical cavity, etc. For example, a dosimetric plan may indicate position, quantity, radioactive strength, etc., for placement of radioactive carriers on a treatment surface of a patient, such as in view of characteristics of a tumor removed (or planned for removal) from the patient. In some embodiments, dosimetric plans may include shielding specifications (or a "shielding plan), such as characteristics of an isolation sheet (e.g., any of the various characteristics associated with treatment materials, shielding layers, and/or isolation sheets discussed herein) to be used on a patient after implantation of the radioactive carriers according to the dosimetric plan. In other embodiments, the dosimetric plan for a patient may not include shielding specifications and, for example, may leave determination of the shielding specifications to another specialist, such as a surgeon that implements the dosimetric plan. Thus, the shielding specifications may be determined based on clinical need, even in real-time as or after the prescribed radioactive carriers are positioned on the treatment surface. Determining shielding specifications based on clinical need may better accommodate actual clinical condition of a patient that may be unknown and/or change after creation of a dosimetric plan, such as after removal of a tumor. In some embodiments, clinical need may be considered in order to increase shielding around sensitive tissue areas (e.g., an optic nerve, vital organs, etc.), place isolation sheet(s) on scar tissue areas, resize isolation sheet(s) to better fit a surgical cavity, and/or other clinical conditional. In some embodiments, shielding specifications may be determined based on a dosimetric plan in view of clinical need of the patient at the time of insertion of the prescribed radiation sources. Any discussion herein of determining shielding specifications according to a dosimetric plan, which is one type of "treatment plan" specific to radiation therapy planning, refer additionally to determination of those same shielding specifications according to clinical need, such that shielding specifications may be determined based on a dosimetric plan and/or clinical need.

Therapeutic Index: relationship between an amount of therapeutic effect provided by a therapeutic agent, such as one or more radioactive seeds in carriers, to an amount that causes toxicity. The therapeutic index may indicate a relative amount of healthy tissue (non-target tissue) receiving radiation (e.g., above a certain dosage level) compared to an amount of the target area (e.g., a tumor or tumor bed) receiving radiation. The therapeutic index may be a ratio of radiation delivered to a treatment area (e.g., tumor or tumor bed) to radiation delivered to areas surrounding the treatment area. Thus, a higher therapeutic index generally indicates better localization of radiation to the treatment area, sparing as much of the surrounding area from radiation as possible. Accordingly, improving the therapeutic index may increase local control of tumors and/or decrease the morbidity of treatment.

Example Carriers

Figure 1B:
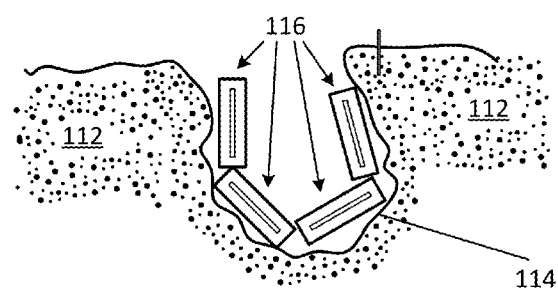

FIGS. 1A and 1B are cross-sectional drawings illustrating a portion of patient tissue 102 and 112 having tumor beds 104 and 114 therein, respectively. These tumor beds 104 and 114 may have been created by a surgical process, such as a tumor debulking process that removed tumor cells. For example, the tissue 102 or 112 may represent cranial tissue of a human (or other mammal) wherein the tumor beds 104 and 114 are surgically created in order to remove one or more tumors from the brain (and/or surrounding areas) of the patient. Thus, the tissue 102 and 112 may represent different types of material, such as bone, fatty tissue, brain tissue, etc. Any reference herein to "tissue" may reference to any type of mammalian material, including bone, fatty tissue, brain tissue, etc.

In the example of FIG. 1A, four tile carriers 106 are illustrated as already placed within the tumor bed 104. Placement of the tiles 106 in the tumor bed 104 may occur in the surgical room, such as immediately after a surgical procedure, or elsewhere at some time after the surgical procedure, such as in a separate procedure performed hours, days, or weeks later. In the embodiment of FIG. 1A, the tiles 106 are pliable such that they conform to the treatment surface, which is the non-planar outer surface of the tumor bed 104 in this example. In one embodiment, the tiles 106 may comprise collagen that provides such flexibility in conforming the tiles 106 to a nonplanar surface. In the example of FIG. 1B, tiles 116 that are placed in tumor bed 114 of tissue 112 are comprised of a non-pliable substrate, such as a polymer, that maintains its substantially planar shape even when placed within the tumor bed 114. For ease of discussion, tile carriers discussed herein are illustrated as being flexible, such as the tiles 106 in FIG. 1A. However, any other type of tile carrier, as well as other configurations of carriers, such as gore, star, or dot carriers, may be used alternatively. Thus, any discussion herein of a tile carrier or any other particular carrier should be interpreted to also include embodiments using other types of carriers, no carriers at all (e.g., radioactive seeds could be placed in a tumor bed without first being placed in a carrier), and/or any other radiation delivery device.

Figure 1C:
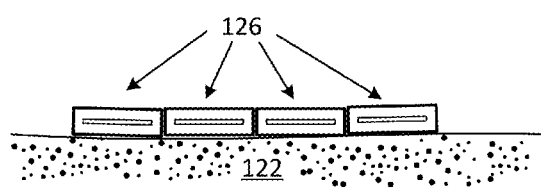

In the examples of FIGS. 1A and 1B, the tiles 106 and 116 each include a radioactive seed embedded therein. As discussed in the related patents and patent applications noted above, the radioactive seeds can have various shapes, sizes, and characteristics. In the examples discussed herein, radioactive seeds are illustrated as generally cylindrical, such as the cylinders included in each of the tiles 106 and 116 of FIGS. 1A and 1B. However, other shapes and sizes of seeds may be used in other implementations. In the examples discussed herein, radioactive seeds are substantially rigid, such that they maintain their shape within their respective carriers. Thus, as shown in FIG. 1A, even when the carriers 106 near the bottom of the tumor bed 104 are deformed to better engage with the treatment surface, the seeds therein retain their linear cylindrical shape. In other embodiments, seeds may be more pliable, such that they are somewhat malleable in taking on a shape of a specific treatment surface. In the example of FIG. 1C, a tumor cavity is not present and, thus, the carriers 126 are placed on a substantially planar treatment area of tissue 122, such as a patient's skin covering the skull or other tissue.

In the examples of FIGS. 1A, 1B, and 1C radiation is delivered to the corresponding treatment area by the radioactive seeds within the carriers 106, 116, and 126, respectively. However, radiation from these seeds may also extend to other areas of tissue that are outside of the desired treatment area. For example, radiation emitted from top surfaces of the carriers may extend to surrounding tissue outside of the treatment area, other portions of tissue that come near and/or contact the treatment surface (e.g., the hand of a patient placed over the tumor bed 104), or even tissue of another person or animal, such as a spouse that lays near the treatment surface and, thus, receives radiation from the radioactive seeds. Accordingly, depending on placement of the carriers, size and shape of treatment surface, radioactive seed intensity, and/or many other factors, the therapeutic index for use of such carriers may be unnecessarily low. Discussed herein are various shielding devices, systems, and methods, which are generally designed to improve therapeutic index for delivery of radiation using brachytherapy.

Example Isolation Sheets

Disclosed herein are several embodiments of isolation sheets, which are generally any materials that are placed over and/or that are included within radioactive carriers in order to provide radioactive shielding. As noted above, an isolation sheet may include a single shielding layer, which itself includes one or more shielding materials, or multiple shielding layers in various positional relationships to one another. Isolation sheets may improve a therapeutic index associated with a dosimetry plan. Shielding materials used in isolation sheets may be may include, for example, high-z material or alloy thereof, in various forms, formed in shielding layers such as a foil, mesh, rods, cylinders, bars, dots, spheres, oriented strips, grid, embedded, sprayed, bio-adhered, or an on-lay in or on a substrate, such as one or more layers of collagen. While specific shapes, material compositions, properties, etc. are disclosed herein with reference to various example isolation sheets, variations on these examples are anticipated.

In one embodiment, a shielding apparatus comprises a collagen substrate and a plurality of shielding materials embedded in the collagen substrate, the shielding materials each comprising a high-z material, wherein the shielding materials are positioned within the collagen substrate to match positions of a corresponding plurality of radiation sources arranged according to a dosimetric plan, at least some of the radiation sources arranged with gaps between the at least some of the radiations sources and adjacent of the plurality of radiation sources. In some embodiments, when the apparatus is placed on the plurality of radiation sources, each of the shielding materials provides substantial shielding of radiation emitted by a corresponding radiation source and reduced shielding of radiation from other of the plurality of radiation sources, and gaps between respective shielding materials provide less distortion of magnetic energy than the shielding materials.

In some embodiments, gaps comprise collagen of the collagen substrate between shielding materials. In some embodiments, substantial shielding shields more than 80% of radiation. In some embodiments, reduced shielding shields less than 50% of radiation. In some embodiments, the one or more shielding materials are formed in the shape of rods, cylinders, or spheres.

In some embodiments, the dosimetric plan indicates x*y radiation sources arranged in x rows and y columns, and the collagen substrate is embedded with x*y shielding materials in x rows and y columns. In some embodiments, the dosimetric plan indicates a gap distance between adjacent radiation sources in each of the x rows, and the shielding materials in each of the x rows are spaced apart by the gap distance. In some embodiments, the dosimetric plan indicates a second gap distance between adjacent radiation sources in each of the y columns, and the shielding materials in each of the y columns are spaced apart by the second gap distance.

In some embodiments, the dosimetric plan indicates an irregular arrangement of the plurality of radiation sources, and the shielding materials are positioned in the same irregular arrangement in the collagen substrate.

In some embodiments, the shielding apparatus is sufficiently malleable to be formed into a substantially hemispherical shape within a corresponding substantially hemispherical cavity, while in other embodiments, the shielding apparatus is configured for attachment on either side of a substantially hemispherical cavity such that an air-filled void is formed between a bottom of the hemispherical cavity and the formed into a substantially hemispherical shape within a corresponding hemispherical cavity.

In some embodiments, the collagen substrate is adhered to a bio-compatible material.

Figures 2A, 2B:
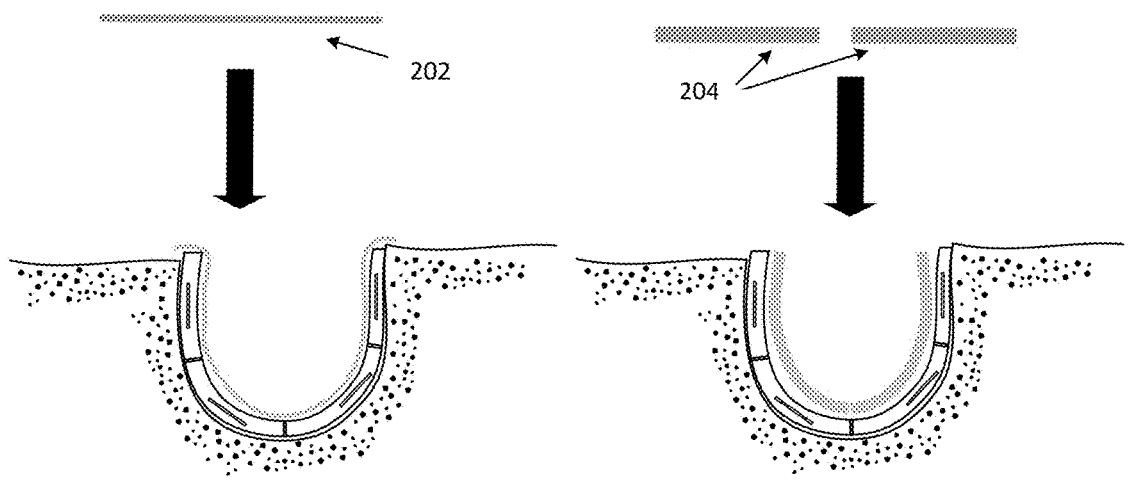
FIG. 2A-2G illustrates various treatment surfaces with carriers placed thereon, and including one or more isolation sheets.

FIG. 2A illustrates a tumor cavity having four carriers, each embedding one or more radioactive seeds, placed therein. In this embodiment, the carriers are pliable such that they substantially engage the treatment surface. In this example, a thin isolation sheet 202 comprising a single shielding layer is positioned on (or near) the carriers within the tumor bed and partially extending outside of the tumor bed. For example, the isolation sheet 202 may be pressed down into the tumor bed manually (by a surgeon's fingers, hands, or a surgical tool). In some embodiments, the isolation sheet 202 may be adhered to the carriers using an adhesive property that is inherent to the carrier material and/or a separate adhesive. As noted above, certain carrier materials may have an inherent stickiness that adheres the carriers to the isolation sheet 202. For example, collagen carriers may adhere to the isolation sheet 202 (and/or tissue of the treatment surface on the opposing side) to varying extents, depending on moisture on the isolation sheet 202 and/or carriers.

FIG. 2B illustrates the tumor cavity again having four carriers embedded therein, but now with two thicker isolation sheets 204 (each comprising a single shielding layer and/or multiple stacked shielding layers) overlaid thereon to provide radiation shielding (and to improve therapeutic index). In other embodiments, a single thicker isolation sheet may be used. Similar to discussion above with reference to FIG. 2A, the isolation sheets 204 may be placed on or near the carriers (e.g. inserted into the tumor cavity or covering an opening of the tumor cavity) in various matters and may be adhered to the carriers (either before or after insertion onto the treatment surface) in certain embodiments.

Figures 2C, 2D:
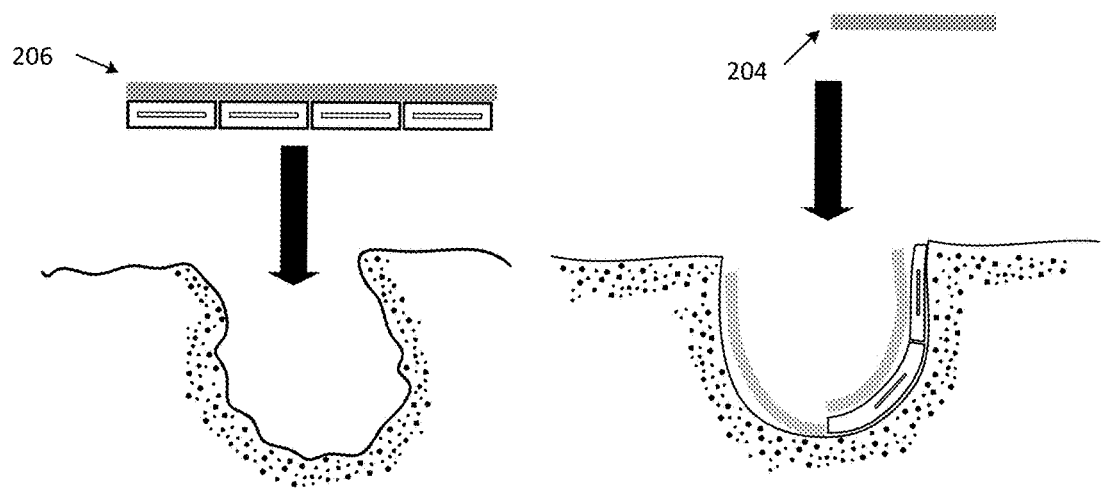

FIG. 2C illustrates an isolation sheet 206 that is adhered to carriers prior to insertion into a tumor bed. Depending on the embodiment, the isolation sheet 206 may be adhered using various adhesives, such as a medical grade adhesive. In this embodiment the isolation sheet 206 may maintain attachment to the carriers better than when adhered within a tumor cavity.

FIG. 2D illustrates one of the isolation sheets 204 placed in a tumor cavity to cover two radioactive carriers in order to provide shielding of radiation from those carriers. In this example, a separate isolation sheet is placed directly on adjacent tissue (tissue outside of the treatment area), such as to reduce or prevent radiation from entering the surrounding area. For example, in the tumor cavity of FIG. 2D, the tumor may have been entirely and/or primarily on the right side of the resultant tumor cavity, such that radioactive carriers are placed only on that side. However, in order to increase the therapeutic index of a post-operative radiation treatment plan, an isolation sheet can also be placed nearby the radioactive carriers on non-treatment tissue in order to shield that surrounding tissue from radioactivity.

In a similar way as the isolation sheet in FIG. 2D is placed directly on tissue outside of the treatment surface, in some embodiments a shielding material may be placed directly on such tissue and/or on radioactive carriers in place of an isolation sheet. Any discussion herein of an isolation sheet similarly could include a shielding material that is not formed into an isolation sheet, but is rather applied directly to the treatment surface or area adjacent to the treatment surface. For example, calcium phosphate (e.g., that is 95% resorbed in 26-86 weeks) or Calcium Sulfate (that resorbs in 4-12 weeks) may be provided as an injectable paste such that a layer could be "painted" where needed to provide shielding. Such a shielding material may be advantageously used where an isolation sheet may not be practicable, such as extradural deep to suture lines. Such isolation materials may provide a bone-graft analog, as discussed in "Bone-graft substitutes in orthopaedic surgery," by Jahangir et al. (Published January, 2008 and available for download at http://www.aaos.org/news/aaosnow/jan08/reimbursement2.asp), which is hereby incorporated by reference in its entirety and for all purposes.

Figure 2E:
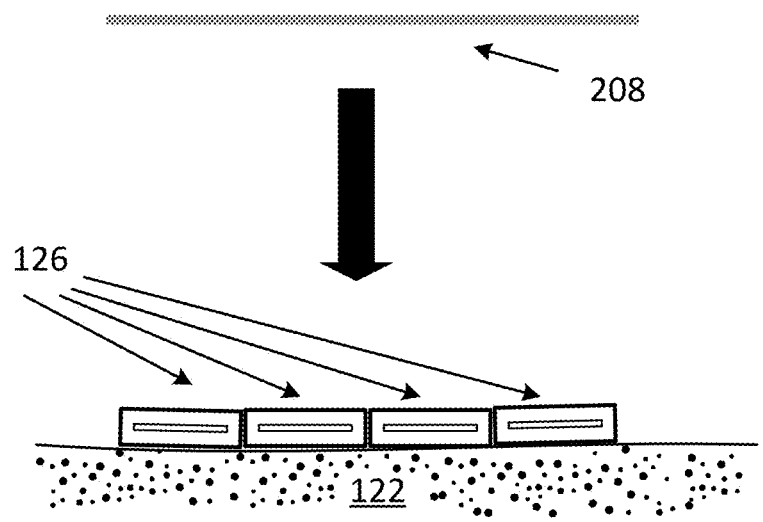

FIG. 2E illustrates four radioactive carriers 126 placed on a treatment surface that is substantially flat, above a treatment area of tissue 122. As discussed elsewhere herein, isolation sheets may be applied to any treatment surface, whether substantially hemispherical, irregularly shaped, substantially planar, or any other shape. In the example of FIG. 2E, an isolation sheet 208 (which may include any shielding layer or combination of shielding layers discussed herein, such as those discussed with reference to FIG. 4) is selected for placement atop the radioactive carriers 126.

Figure 2F:
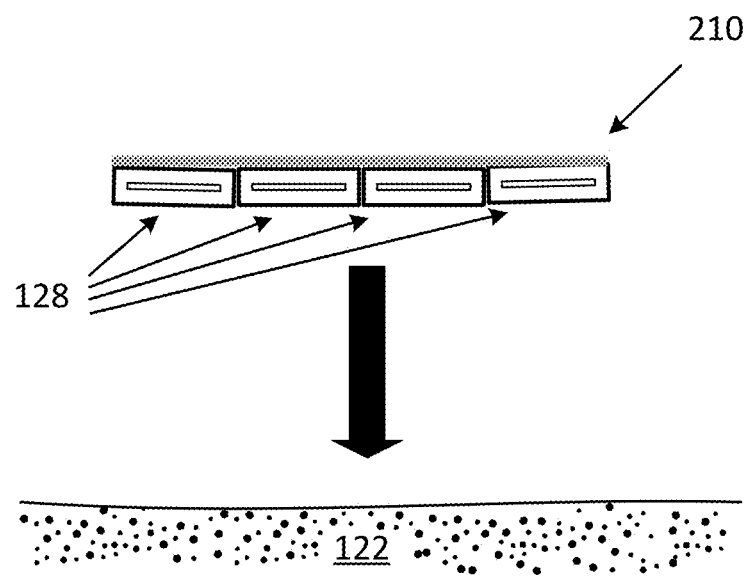

In the example of FIG. 2F, an isolation sheet 210 is adhered to carriers 128 prior to placement on a treatment area of tissue 122. As discussed elsewhere herein, the carriers 128 may be adhered to the isolation sheet 210 via a separate adhesive compound or material, or via adhesive properties of one or more of the isolation sheet 210 and/or carriers 128.

Figure 2G:
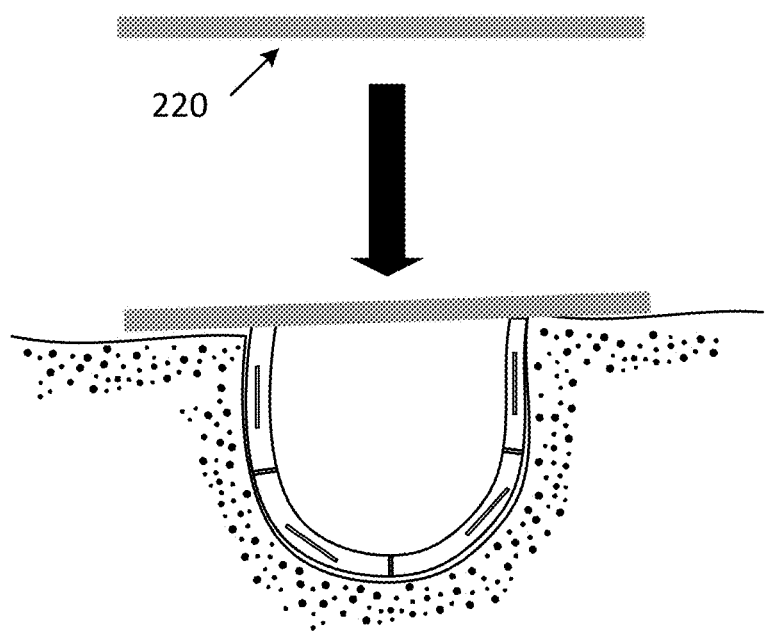

In the example of FIG. 2G, an isolation sheet 220 is placed over a treatment surface such that it is not directly contacting the carriers (except possibly end portions of the end carriers). Positioning an isolation sheet in this manner may be easier for the surgeon (than manipulating an isolation sheet into an irregular shaped cavity), less painful for the patient, and/or may provide similar amounts (or at least sufficient amounts) of radiation shielding as an isolation sheet that is manipulated into a tighter fit within a surgical cavity, such as in the example of FIG. 2A. In applications where the treatment area is a patient's brain, this isolation sheet placement may be referred to as extracranial, denoting its placement outside of the cranium. Such extra-cavity placement of isolation sheets is possible with any of the isolation sheets discussed herein. In some embodiments, extra-cavity placement allows thicker and/or more shielding materials, which generally cause more rigidity of the isolation sheet, to be used and more easily positioned outside the surgical cavity.

FIGS. 3A-3D are top views illustrating example dimensions and shapes of isolation sheets. The illustrated sizes and shapes are examples only—any other shapes or dimensions are contemplated by this disclosure. Thicknesses of these example isolation sheets are not illustrated in these figures, but example thicknesses and materials of isolation sheets are illustrated in FIG. 4. Thicknesses of these example isolation sheets, which each include one or more shielding layers (which each include one or more shielding materials, such as in a shielding layer substrate), range from 0.05 mm to 8 mm in thickness, or maybe even thicker (e.g., 10-20 mm) in other applications. Depending on the embodiment, and as illustrated in the examples herein, thicknesses of isolation sheets may differ from thicknesses of the underlying carriers. For example, the carrier may have a thickness of 4 mm, while an isolation sheet applied to that carrier may have a thickness of only 1 mm. Of course, any other combination of carrier and isolation sheet thicknesses are contemplated herein. Any of the isolation sheets illustrated herein, including those in FIGS. 3A-3D may have any thicknesses, materials, and/or other characteristics discussed herein, such as those in FIG. 4.

Figure 3A:
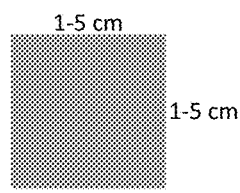
FIGS. 3A-3D are top views illustrating example dimensions and shapes of isolation sheets.

In the example of FIG. 3A, a square isolation sheet having sides of a length from 1-5 cm is shown. For example, the isolation sheet may have sides that are each one centimeter. In other embodiments, a similar isolation sheet may be rectangular, such as having dimensions of 1 cm×5 cm.

Figure 3B:
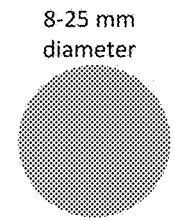

The example of FIG. 3B is a circular isolation sheet having a diameter of between 8-25 mm. Thus, example circular isolation sheets may have diameters of 10 mm, 15 mm, 20 mm, 25 mm, etc.

Figure 3C:
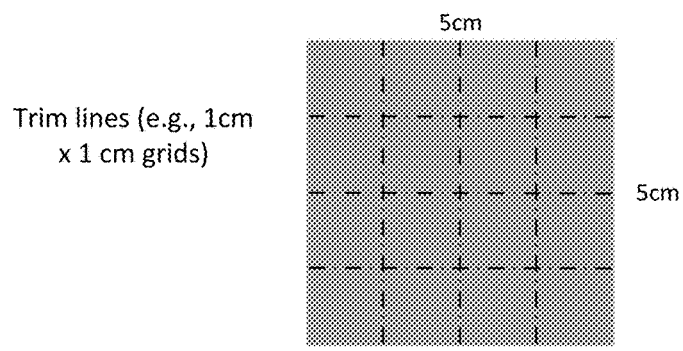
Figure 3D:
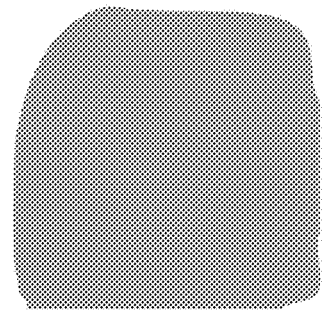

The example isolation sheet of FIG. 3C is a 5 cm×5 cm isolation sheet that includes trim lines at one centimeter intervals. As noted elsewhere herein, isolation sheets may comprise materials (e.g., shielding materials and/or substrate materials) that allow adjustment of size of the isolation sheet and/or creation of multiple smaller isolation sheets from a single sheet. For example, an isolation sheet may be trimmed using scissors, razor blade, knife, or similar cutting implement, to create a custom shaped isolation sheet, such as the irregularly shaped isolation sheet illustrated in FIG. 3D, which may be created by cutting the example isolation sheet of FIG. 3C.

Using the trim lines in the example of FIG. 3C, a user can accurately create multiple isolation sheets having dimensions anywhere between 1 cm-5 cm on either side. For example, a user could create four 1 cm×5 cm isolation sheets, two 2 cm×5 cm isolation sheets, or sixteen 1 cm×1 cm isolation sheets from the isolation sheet of FIG. 3C. In other embodiments, trim lines may be placed at different intervals. In one embodiment, trim lines may be generated by a dosimetric planning software, such as the software discussed in U.S. patent application Ser. No. 15/017,461, entitled "Radioactive Implant Planning System and Placement Guide System," filed on Feb. 5, 2016, which is hereby incorporated by reference in its entirety. For example, in order to achieve a maximum therapeutic index, a custom shaped isolation sheet or multiple isolation sheets may be determined by software and implemented by the user. In one embodiment, the software generates a printout of the trimming pattern that can be overlaid on an isolation sheet so that the printed trimming pattern as well as the isolation sheet thereunder can be simultaneously trimmed in order to achieve the calculated isolation sheet size, shape, pattern, etc.

Figure 4A:
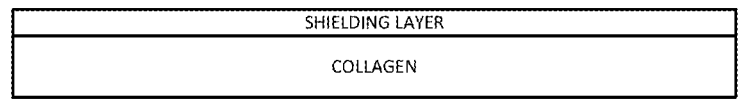
FIGS. 4A-4I illustrate cross sections of isolation sheets, including indications of example materials and material dimensions.
Figure 4B:
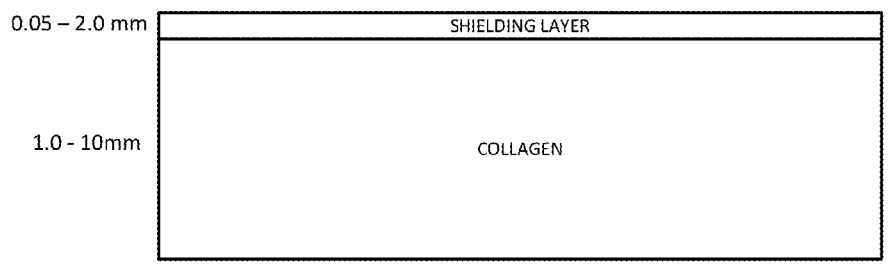

FIGS. 4A-4I illustrate cross sections of isolation sheets, including indications of example materials and material dimensions. The isolation sheets are illustrated such that the bottom surface of each isolation sheet is placed onto (or near, such as in an extra-cavity placement) radioactive carriers. For example, the collagen layers in FIGS. 4A and 4B are configured for placement onto radioactive carriers, with the shielding layer separated from the radioactive carriers by collagen. Isolation sheets of any shape or size, such as those discussed above with reference to FIG. 3, for example, may include shielding and non-shielding layers similar to those illustrated in one or more examples in FIGS. 4A-4I, or combinations of layer components or layer thicknesses. In many embodiments, one or more layers of collagen, or some other bio-compatible spacing material, may be used in conjunction with a shielding layer in order to provide distance between the radioactive materials in carriers and the shielding layers of an isolation sheet. Depending on characteristics of shielding materials, such as radiation shielding ability, replacement of a shielding layer by a shielding layer having a different shielding material may necessitate use of the thicker (or thinner) shielding layer in order to achieve the desired shielding goals (e.g., a minimum radiation shielding). For example, a high-z metal foil shielding layer of thickness 0.05 mm provides higher radiation shielding than a non-metallic polymer shielding layer of thickness 0.05 mm. Thus, to maintain similar radiation shielding with the non-metallic shielding layer may require a thickness of 2 mm or more.

Figure 4C:
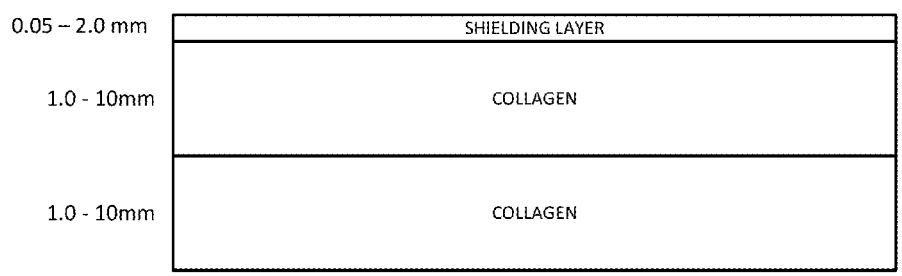
Figure 4D:
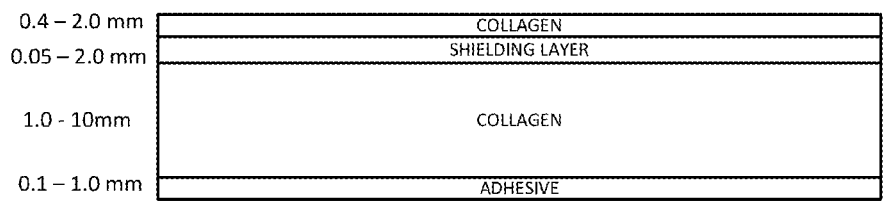

The examples of FIGS. 4A-4D include shielding layer comprising a substantially uniform composition, such as a foil or polymer sheet of a shielding material. FIGS. 4E-4H include shielding materials that are interspersed within a shielding layer substrate, such as high Z or other shielding materials that may be interspersed within a collagen layer. FIG. 4I illustrates an isolation sheet having a combination of a uniform composition shielding layer (e.g., a high Z metal foil layer) and a dispersed composition shielding layer (e.g., small fragments of a dense nonmetallic material interspersed within a collagen layer), along with a collagen layer on each side of the shielding layers.

Any examples herein of a shielding layer may include a uniform composition and/or a dispersed composition of shielding materials within a shielding layer substrate, even where specific other examples of shielding layers are discussed. As noted elsewhere, layers of shielding layers discussed herein may be adhered using a separate adhesive material, by properties inherent in one or more of the layers (such as wetted collagen, for example), or may not be adhered together (e.g., they may be placed adjacent to one another, but not adhered to one another). Thus, any discussion of shielding layers of an isolation sheet herein that does not mention adhesives may be modified to include separate adhesive materials and/or layers.

The appropriate combination of an absorptive material, such as collagen, and a reflective material, such as a metallic foil, to include in a shielding layer and/or multiple shielding materials, spacing materials, etc. of a shielding layer and/or an isolation sheet including multiple shielding layers, may be incorporated into a dosimetric plan for a particular radiation treatment. For example, if a dosimetric plan benefits from radiation being reflected back towards the treatment area, a layer of collagen separating the carrier(s) and the reflective material may be minimal or zero (e.g., zero—2 mm), while if absorption of radiation from the carrier(s) is more desirable, a larger absorptive layer may be implemented, such as a 10-30 mm layer of collagen underneath a reflective shielding layer (or without a reflective material layer). In some embodiments, multiple shielding layers and/or isolation sheets having different combinations of absorptive and reflective materials may be used in a single treatment plan, such that radiation from certain carriers within the treatment plan is primarily reflected back towards a treatment area, while radiation from other carriers within the treatment plan is primarily absorbed by the adjacent isolation sheets.

In the example of FIG. 4A, the isolation sheet includes a single collagen layer and a shielding layer, such as comprising a uniform composition shielding material having a high Z material and/or a dense nonmetallic material. Similarly, the isolation sheet in the example of FIG. 4B includes a collagen material having a thickness of between 1.0-10 mm combined with a shielding layer having a thickness of between 0.05-2.0 mm. The example isolation sheet of FIG. 4C includes two collagen layers that are configured to separate radioactive carriers from a shielding layer. In this embodiment, the multiple collagen layers may be used in view of an increased availability, reduced cost, and/or other factors, of a thinner collagen layer than compared to a same thickness of a single collagen layer. In the example of FIG. 4C, each of the collagen layers has a thickness between 1.0-10 mm and the shielding layer has a thickness of between 0.05-2.0 mm. In one embodiment, each of the collagen layers has a same thickness, but in other embodiments collagen layers of different thicknesses may be used. The example of FIG. 4D illustrates an isolation sheet having an adhesive layer configured for attachment to radioactive carriers, such as to adhere the isolation sheet to the radioactive carriers before placement on a treatment surface or in order to adhere the isolation sheet to the radioactive carriers that are already positioned on the treatment surface. In this specific example, the adhesive layer having a thickness of between 0.1-1.0 mm is adhered to a collagen layer having a thickness of between 1.0-10 mm, which is adjacent to a shielding layer having a thickness of between 0.05-2.0 mm, and finally a collagen layer having a thickness of between 0.4-2.0 mm.

In the examples of FIG. 4E-4H, shielding layers are shown with various shielding materials, which may include fragments, particles, pieces, and/or solutions, of high Z and/or nonmetallic materials, that are interspersed within a shielding layer substrate. For example, the shielding layer substrate may be a collagen or similar bio compatible material with suitable properties that is capable of holding or incorporating a shielding materials, such as particles of a high Z material (e.g., an alloy, nanoparticle or mixture thereof) and/or a non-metallic high density material (e.g., calcium carbonate, calcium sulfate, barium sulfate, zirconium dioxide, polymers and polymer hybrids of these and other materials as may best fit the need). Such shielding materials may advantageously provide increased tumor bed conformation (e.g., in view of the flexible nature of collagen and similar substrates) and/or improved intraoperative handling properties over uniform composition shielding materials alone.

Depending on embodiment, the shielding materials may be introduced into the shielding layer substrate, e.g., a biocompatible substrate, by infusion, soaking, suffusion, pressure inducement, absorption, electroporation, lypholization or other means on or into the lattice structure of, within, or between the interstices of the substrate, in order to form a shielding layer. For example, a collagen substrate, which has properties similar to a sponge when wetted (with minimal or no swelling of the collagen), may absorb shielding materials, such as a liquid calcium carbonate solution. Once such a shielding solution has been soaked into the collagen substrate, a sealing layer, such as a hydrophobic polymer layer, may be overlaid on the shielding material in order to reduce risk of leakage of the shielding solution when the infused collagen substrate later encounters moisture (e.g., either by preventing moisture from being absorbed by the collagen or preventing leakage of the shielding solution from wetted collagen). In other embodiments, shielding materials (e.g., particles and/or solutions) may be interspersed within a shielding layer substrate in other matters, such as by placing particulars of shielding materials atop a substrate and then heating the substrate to allow the shielding materials to move within the substrate. Any other method of embedding shielding materials and/or solutions is also contemplated. In one embodiment, a shielding layer including interspersed metallic particles may entirely or substantially avoid heating issues that would otherwise be created by, for example, MRI-induced heating. In some embodiments, shielding materials may be introduced into only a portion of a shielding material substrate, such as into a top 2 mm portion of a collagen substrate having a total thickness of 4 mm, such that the lower 2 mm of the collagen substrate do not include shielding materials and, therefore, provide primarily spacing and/or absorption to the shielding materials infused portion of the substrate.

Figure 4E:
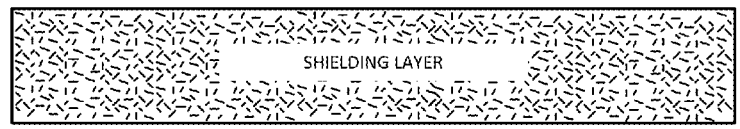
Figure 4F:
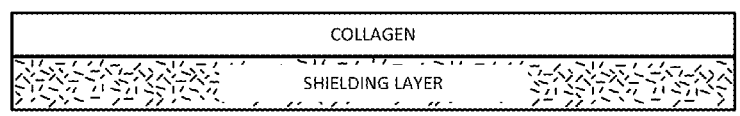
Figure 4G:
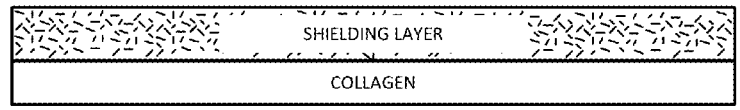
Figure 4H:
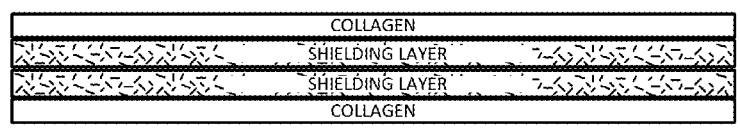
Figure 4I:
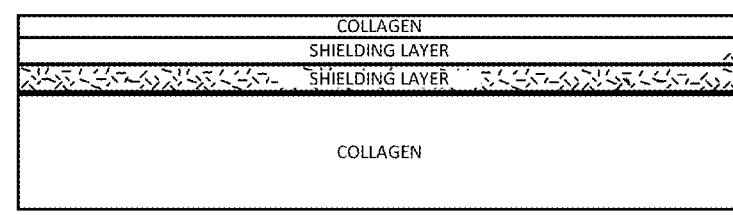

In the example of FIG. 4E, the isolation sheet comprises a single shielding layer having a thickness of between 0.05-1 mm. In the embodiment of FIG. 4F, the shielding layer has a thickness of between 0.4-2.0 mm, and is adjacent a collagen layer having a thickness of between 0.4-2.0 mm. The example isolation sheet of FIG. 4G includes similar components as FIG. 4F (perhaps with varying thicknesses of components within the provided thickness ranges), but with the collagen layer configured for placement onto radioactive carriers and providing a spacing between the radioactive carriers and the shielding layer. In the example isolation sheet of FIG. 4H, two shielding layers, each having a thickness of between 0.05-1.0 mm (perhaps different thicknesses) are placed between collagen layers having thicknesses of between 0.05-1.0 mm (perhaps different thicknesses).

FIG. 4I illustrates an isolation sheet having a uniform composition shielding layer 494 (e.g., one of the shielding materials discussed with reference to FIGS. 4A-4D, such as a foil) and a dispersed composition shielding layer 496 (e.g., one of the shielding materials discussed with reference to FIGS. 4E-4H or FIGS. 7B-7I), with the combination of shielding layers between collagen layers 492 and 498. In this embodiment, the collagen layer 498 that is placed next to the radioactive carriers has a thickness of between 1.0-10 mm, while the opposite collagen layer 492 has a thickness of between 0.4-2.0 mm. As discussed elsewhere, such layer thicknesses, placement of shielding layers within isolation sheets, and combinations of shielding layers within isolation sheets, are provided as examples—isolation sheets may include various combinations of these elements.

Figure 5:
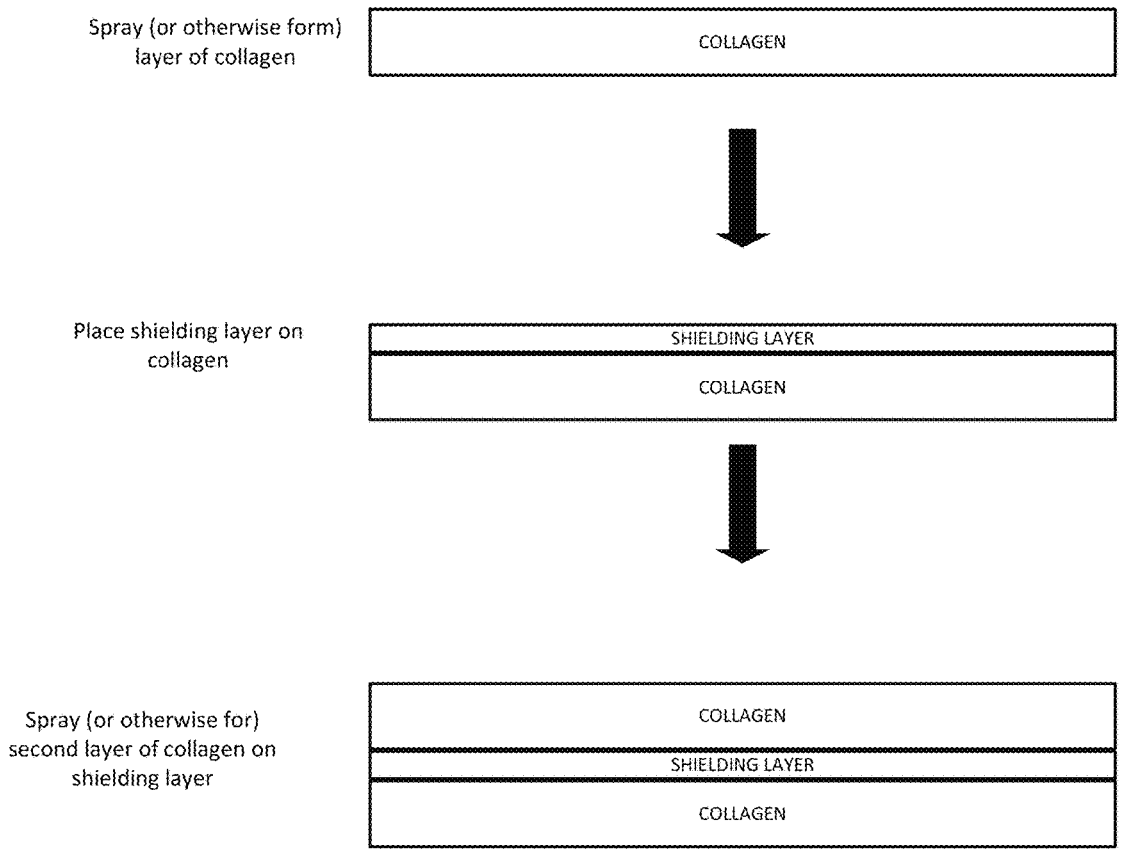
FIG. 5 illustrates an example of manufacturing an isolation sheet.

FIG. 5 illustrates an example of manufacturing an isolation sheet. Other methods of manufacturing isolation sheets having varying layer thicknesses, materials, radioactive shielding properties, etc., are also contemplated. In the example of FIG. 5, a collagen layer is initially formed, such as by spraying a layer of collagen onto a supporting substrate. Next, after the collagen layer is dried, a shielding layer is placed on the collagen. For example, a thin layer of high Z foil may be placed on the collagen or a shielding material may be sprayed onto the collagen to form the shielding layer. Finally, in the example of FIG. 5, another collagen layer is formed on top of the shielding layer, such as by spraying another layer of collagen or placing preformed collagen on the shielding layer. Another example manufacturing process that may be used to forming shielding layers is vacuum forming, which may be used to force a collagen spray or layer against shielding materials in order to embed the shielding materials into the collagen layer. For example, shielding materials may be placed on the vacuum forming device (either directly or on a substrate layer, such as collagen) and then collagen is sprayed over the shielding materials (or a collagen substrate is placed on over the shielding materials), followed by applying the vacuum force in order to pull the collagen layer over the shielding materials, such as while sprayed collagen dries, in order to embed the shielding materials into the collagen. A similar fabrication process may be used with polymer and other biocompatible substrates, rather than collagen.

Figure 6:
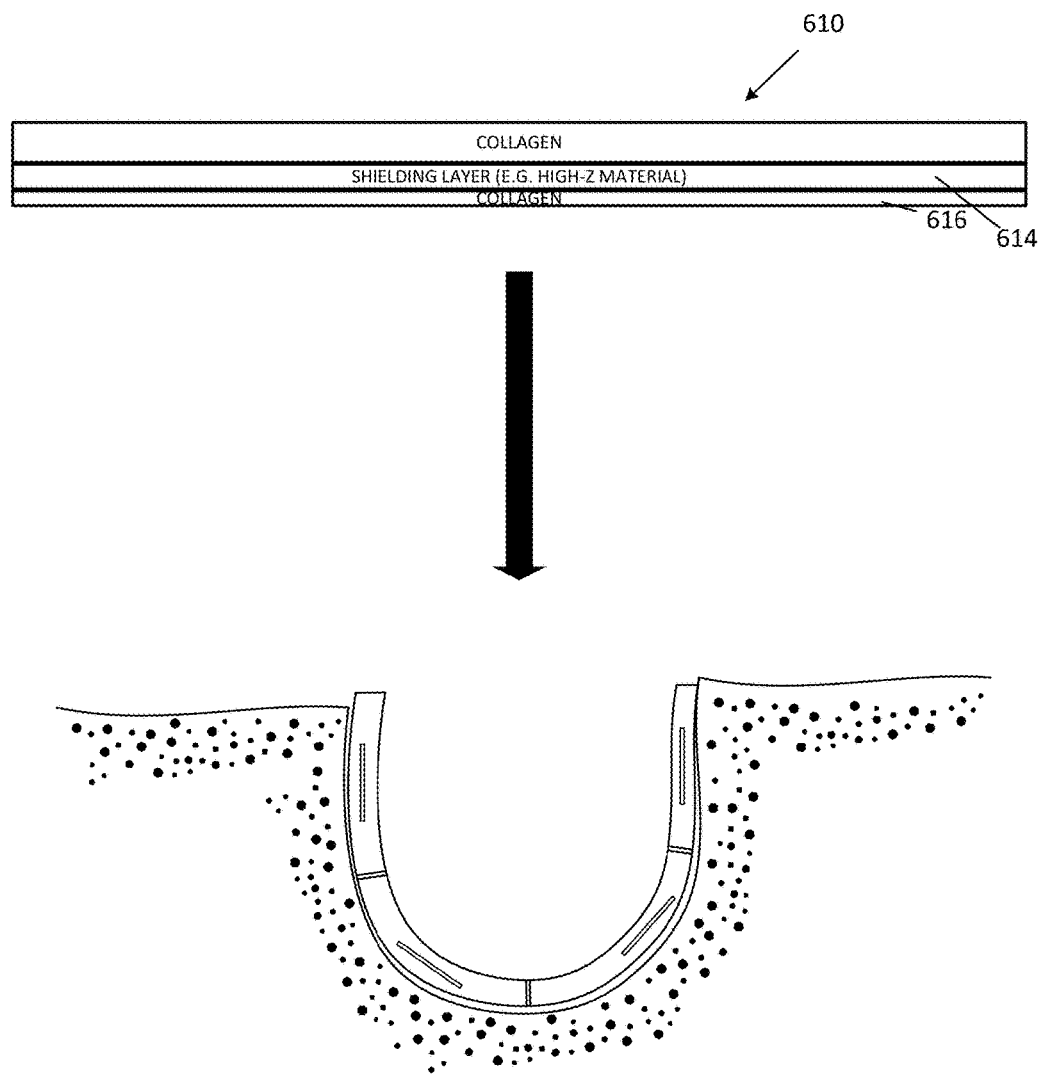
FIG. 6 illustrates an isolation sheet configured to provide backscatter properties that return radioactive particles into a treatment area of tissue.

FIG. 6 illustrates an isolation sheet 610 configured to provide backscatter properties that return radioactive particles into a treatment area of tissue. In some applications, the amount of radiation delivered to a desired treatment area may be increased using an appropriately configured isolation sheet, such as the isolation sheet 610, for example. Isolation sheet 610 includes a thin collagen layer 616, such as having a thickness of between 0.1-1.0 mm adjacent a shielding layer 614 having radiation reflective properties, such as high Z materials. The high Z shielding layer 614 may have a thickness of between 0.05-2.0 mm or more, and the thickness may be configured to meet clinical need (and/or other shielding goals discussed herein), such as by software that generates the shielding specifications. In determining the shielding specifications, components of the radioactive carriers may be adjusted to provide the desired amount of radiation to the treatment area, considering the additional radioactive treatment provided by backscatter of particles that are reflected back towards the treatment area by the high Z shielding material of the shielding layer 614. In other embodiments, multiple high Z shielding layers may be included, such as shielding layers comprising high Z materials that have varying backscatter properties, such that a combination of the shielding materials provides increased backscatter. In the example of FIG. 6, the isolation sheet 610 includes a collagen layer atop the high Z material.

Additional Example Shielding Materials

Figure 7A:
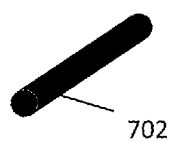
FIG. 7A illustrates three example shielding materials that may be used in various embodiments of shielding layers and corresponding isolation sheets discussed herein.
Figure 7A:
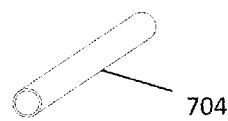
Figure 7A:
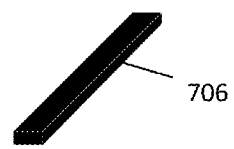

FIG. 7A illustrates three example shielding materials that may be used in various embodiments of shielding layers and corresponding isolation sheets discussed herein. In particular, FIG. 7A illustrates a rod 702, a cylinder 704, and a bar 706. Each of these shielding materials, as well as any other shielding material discussed herein, may be used alone, or in conjunction with other shielding materials as part of an isolation sheet.

The rod 702 and cylinder 704 are each generally cylindrical in shape and may have diameters of from 0.01 mm to 2 mm or more in various embodiments. The rod 702 comprises a solid material, such as any of the metallic or nonmetallic shielding materials discussed herein, while the cylinder 704 includes a cylindrical aperture extending along a length of the cylinder 704. The rod 702 may be referred to as a wire 702 also, especially for smaller diameters. The bar is generally a rectangular prism shape and may be a solid shielding material (as shown in FIG. 7A) or having an elongate aperture along the length of the bar 706. The bar 706s, as well as foils that are discussed herein, may have a thickness from 0.005 mm to 0.5 mm, a width of from 0.1 mm to 10 mm, and a length of more than 10 mm, as needed for the particular application (e.g., according to the particular dosimetric plan). In some implementations, cylinders are hollow, while in others the cylinders are packed with air, fluid, or another solid material, such as to better meet the shielding goals. As noted elsewhere herein, these example shielding materials are exemplary only and do not limit the scope of other shapes, sizes, materials, configurations, etc. of other shielding materials that may be used alone or in the various isolation sheet embodiments discussed herein.

Length of the rod 702, cylinder 704, or bar 706 may vary based on the particular dosimetric plan, such as to provide a prescribed amount of radiation shielding, to allow flexibility sufficient for placement of the resultant isolation sheet (e.g., according to the dosimetric plan), and/or to reduce imaging artifacts and/or heating of the isolation sheet. For example, in order to achieve one or more of these goals, multiple shielding materials, such as rods 702, cylinders 704, and/or bars 706, may be fabricated (or sized after fabrication) to a length that is some fraction of a total length of a shielding layer in which the rods 702 will be placed (e.g., in a shielding layer substrate), such that the multiple rods shielding materials may be spaced apart in the shielding layer to reduce heat generation, for example.

The shielding materials may be used without a substrate, such as by adhering the rod 702 (or cylinders 704, or bars 706, etc.) with a plurality of other similar rods 702 (e.g., using one or more sutures or other biocompatible material to hold the multiple rods next to one another) in order to provide radiation shielding according to a patient's treatment plan. In other embodiments, the shielding materials (e.g., the rod 702, cylinder 704, bar 706, and/or other shielding materials discussed herein), either alone or in combination with other shielding materials, may be embedded or adhered to a shielding material substrate, such as collagen or another biocompatible material, to form a shielding layer.

Additional Example Isolation Sheets

FIGS. 7B-7I provide additional examples of isolation sheets that may be manufactured for use in multiple dosimetric plans and/or may be customize for a particular dosimetric plan. Such customization may be provided by the manufacturer of the isolation sheets and/or may be implemented by a user of the isolation sheets, such as by a surgeon or his staff, in order to better meet the needs of a patient. For example, in some embodiments size of the isolation sheets is adjustable, such as by cutting an isolation sheet with scissors. In some embodiments, isolation sheets include markings that indicate locations of the isolation sheet that are best for cutting (in order to reduce size of the isolation sheet). For example, a grid pattern may be printed on a top surface of an isolation sheet to indicate spaces between shielding material embedded within one or more shielding layers of the isolation sheet.

In some embodiments, the combination of shielding materials (e.g., rods vs. cylinders vs dots, etc., as well as dimensions of the shielding materials, such as width, diameter, length, cross-sectional profile, etc.), material of the shielding materials (e.g., high-Z material vs. polymer material), and/or pattern of the shielding materials within a substrate of an isolation sheet may be selected in order to provide at least the minimum radiation shielding called for in the dosimetric plan, to meet clinical needs of the patient, and/or to meet radiation shielding goals, such as reducing imaging distortion and RF heating of the isolation sheet to a point where imaging of the treatment area of the patient is not effective and/or the isolation sheet puts the patient at risk of burning. Other factors, such as malleability of the isolation sheet, especially with reference to a treatment cavity that requires significant reshaping of an isolation sheet, may be considered in determining these various attributes of an isolation sheet. Such factors, which may be referred to herein as goals, may be included in a treatment plan of a patient (e.g., a dosimetric plan developed by a radiation oncologist), may be determined or adjusted by other physicians, such as the surgeon, in order to meet clinical needs of the patient (e.g., at the time of placement of the isolation sheet), and/or may be determined to meet hospital, municipal, government, and/or patient requirements. In some embodiments, shielding specifications, such as those discussed above, are automatically determined by software executing on a computing system, which considers various shielding goals (e.g., provided by a user or set to default minimum requirements), as well as patient characteristics (e.g., tumor area, cavity dimensions, vital organs or other areas near the tumor area, medical images of the patient, patient history, etc.) in determining shielding specifications for the patient.

In some embodiments, shielding materials (e.g., rods, bars, dots, etc.) are sized and positioned in one or more shielding layers of an isolation sheet to line up with radiation sources onto which the isolation sheet is to be placed. In such embodiments, each shielding material may provide direct blocking of radiation for a particular radiation source. In other embodiments, the shielding materials on an isolation sheet may not directly correspond to and/or line up with the underlying radiation sources. Examples of various configurations of such isolation sheets are provided below.

The various views of the example isolation sheets (e.g., top, side, and end views) represent relative relationships between shielding materials within one or more shielding layers, and are not necessarily to scale with one another.

FIGS. 7B-7I each illustrates multiple views of example isolation sheets, including top view, one or more side views, and one or more end views. In other embodiments, the isolation materials illustrated may be spaced differently than illustrates, such as to provide additional shielding of one portion of the isolation sheet over another portion of the isolation sheet. The example isolation sheets are illustrated with reference to corresponding shielding layer substrates (e.g., substrate 701 of FIG. 7B), which may comprise any available substrate, such as collagen or other biocompatible material in which the shielding materials are embedded. In other embodiments, the shielding layer substrate does not embed the shielding materials, but holds the shielding materials in fixed positions with reference to one another. For example, a shielding layer substrate may comprise an adhesive backed substrate (e.g., a sheet of paper with a biocompatible adhesive on one side) onto which the multiple shielding materials are adhered and held into place with reference to one another. As discussed elsewhere herein, multiple shielding layers using various shielding layer substrates may be used in combination in various isolation sheets.

Figure 7B:
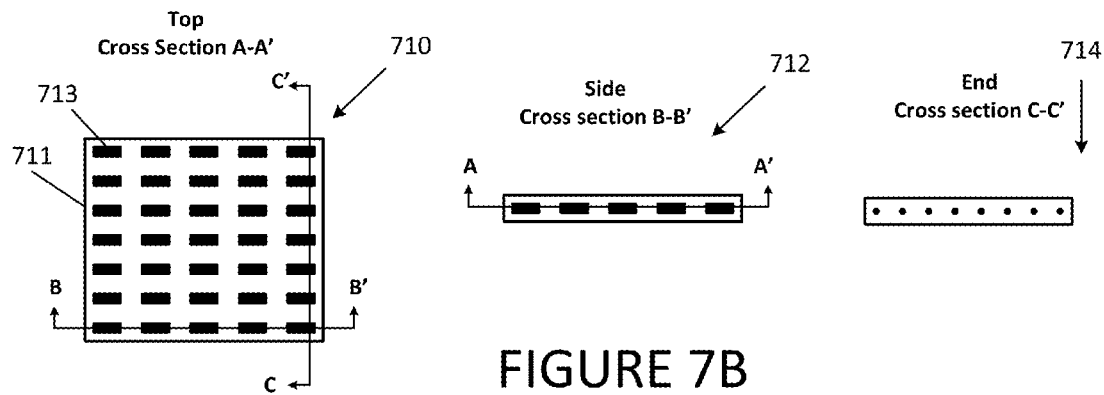
FIGS. 7B-7L provide additional examples of isolation sheets that may be manufactured for use in multiple dosimetric plans and/or may be customize for a particular dosimetric plan.

In the example isolation sheet of FIG. 7B, multiple rods 713 are spaced uniformly with reference to one another in a shielding layer substrate 711. In this example, the rods 713 are arranged in seven rows and five columns, with an equal space between each row and an equal space between each column. In other embodiments, any other number of rows, columns, or other arrangement of rods, may be used, such as to meet one or more requirements of a patient's treatment plan. As shown in the side cross-section view 712, the rods are centered within the shielding layer substrate 711. However, in other embodiments, the rods may be offset within the shielding layer substrate 711, such as to provide more (or less) spacing between the radiation sources (e.g., carriers loaded with radioactive seeds) and the shielding materials. In this example, the rods have a substantially circular cross-section, as shown in view 714, but in other embodiments rods 713 may have varying cross-sectional profiles, such as triangular, pentagon hexagonal, etc.

Figure 7C:
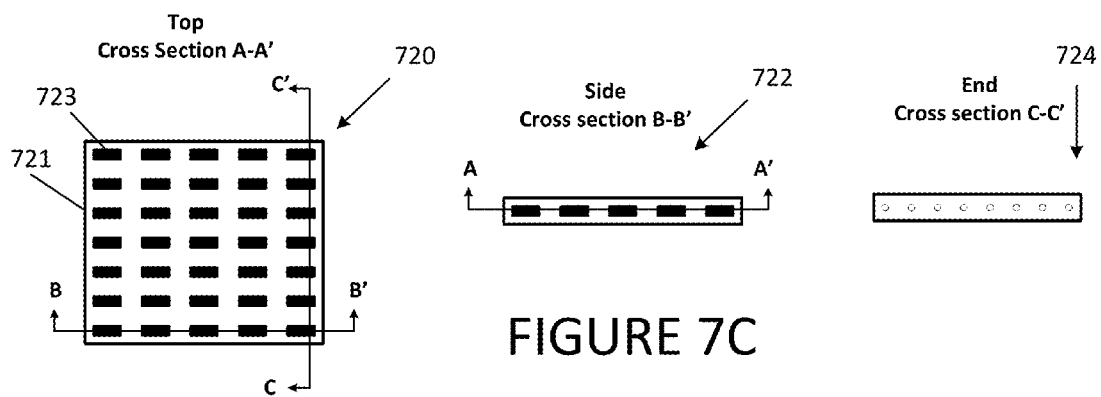

In the example isolation sheet of FIG. 7C, multiple cylinders 723 are spaced uniformly with reference to one another in a shielding layer substrate 721. In this example, the cylinders 723 are arranged in seven rows and five columns, with an equal space between each row and an equal space between each column. In other embodiments, any other number of rows, columns, or other arrangement of cylinders, may be used, such as to meet one or more requirements of a patient's treatment plan. As shown in the side cross-section view 722, the cylinders are centered within the shielding layer substrate 721. However, in other embodiments, the cylinders may be offset within the shielding layer substrate 721, such as to provide more (or less) spacing between the radiation sources (e.g., carriers loaded with radioactive seeds) and the shielding materials. In this example, the cylinders have a substantially circular cross-section and a cylindrical aperture extending through a length of the cylinders, as shown in view 724. In other embodiments, cylinders (e.g., the outer surface of the cylinders 723) and/or the aperture of the cylinders (e.g., the inner surface of the cylinders 723) may have varying cross-sectional profiles, such as triangular, pentagon hexagonal, etc.

Figure 7D:
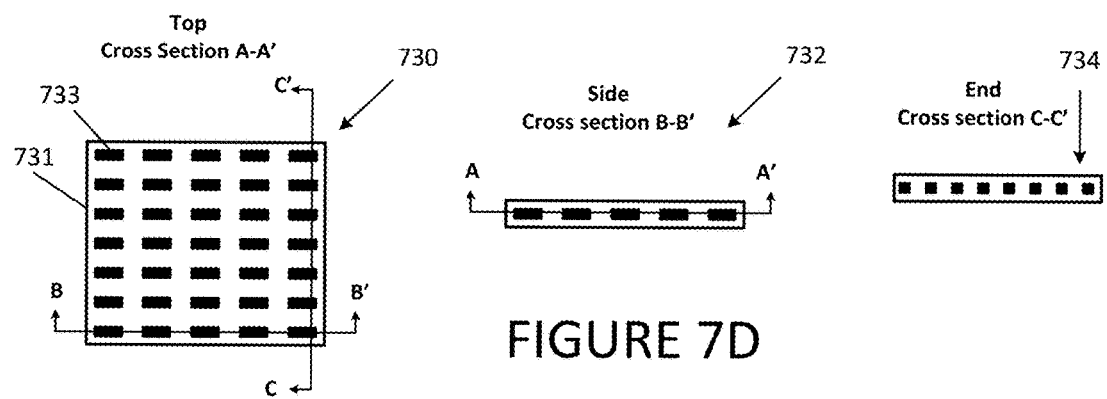

In the example isolation sheet of FIG. 7D, multiple bars 733 are spaced uniformly with reference to one another in a shielding layer substrate 731. In this example, the bars 733 are arranged in seven rows and five columns, with an equal space between each row and an equal space between each column. In other embodiments, any other number of rows, columns, or other arrangement of bars, may be used, such as to meet one or more requirements of a patient's treatment plan. As shown in the side cross-section view 732, the bars are centered within the shielding layer substrate 731. However, in other embodiments, the bars may be offset within the shielding layer substrate 731, such as to provide more (or less) spacing between the radiation sources (e.g., carriers loaded with radioactive seeds) and the shielding materials. In this example, the bars have a substantially rectangular cross-section, as shown in view 734. In other embodiments, bars may have varying cross-sectional profiles, such as triangular, pentagon hexagonal, etc.

In some embodiments, shielding materials (e.g., rods, bars, dots, etc.) are sized and positioned in one or more shielding layers of an isolation sheet to line up with radiation sources onto which the isolation sheet is to be placed. For example, the multiple bars 733 in the example isolation sheet of FIG. 7D may be arranged to correspond to positions of radiation sources (e.g., carriers with radioactive seeds) placed on or near a treatment surface. In this example, this 5×7 set of bars 733 may correspond to a 5×7 set of radiation sources placed in a tumor cavity. Thus, shielding of direct radiation from the radiation sources (e.g., perpendicular to orientation of a seed placed in a horizontal orientation, such as in FIG. 1A-1C) may be most significantly shielded, while radiation emitted at an angle from the radiation sources (e.g., between 60-80 degrees from the longitudinal axis of the seed) may not be shielded as significantly. However, this spaced positioning of the shielding materials to match up with (or "mirror") the underlying radiation sources may provide sufficient overall shielding (e.g., reduce the amount of radiation by more than 25%, 50%, 75%, 90%, or to some acceptable amount of radiation (for example, measures in gray (Gy)) and also provide improved imaging of the patient's anatomy below the shielding materials and/or reduce risk of RF heating (e.g., due to the spaces between the shielding materials). Accordingly, such a one-to-one correspondence of individual shielding materials with individual radiation sources may best meet the shielding goals for some clinical uses. Similarly, a one-to-many relationship of spaced apart shielding materials to radiation sources may provide similar advantages in view of spacing between the shielding materials. For example, with reference to FIG. 7E (discussed further below), each of the 7 elongate rods 743 may correspond to (and be aligned with when placed thereon) multiple radiation sources. For example, each of the elongate rods 743 may correspond to 5 radiation source, such as tiles with embedded seeds, such that the isolation sheet 740 provides shielding of 35 radiation source (5 radiation sources in 7 rows). As discussed herein, radiation source placement within a tumor cavity may be irregular, e.g., not is a rigid row and column arrangement, and, thus, the shielding materials of an isolation sheet may be arranged in a similar irregular arrangement (either based on the dosimetry plan, surgeon's, or other description of planned arrangement of the radiation sources and/or based on actual arrangement of the radiation sources, such as at the time of implantation) of the radiation sources in order to provide similar direct shielding of the radiation sources, while providing some spacing between the shielding materials.

Figure 7E:
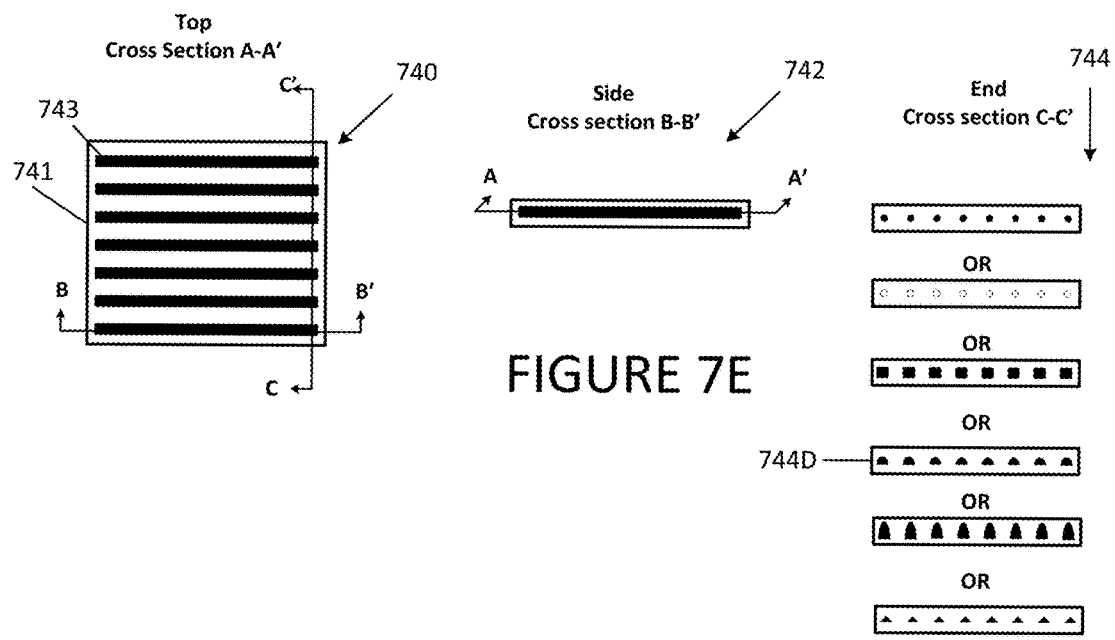

In the example isolation sheet of FIG. 7E, multiple rods 743 are spaced uniformly with reference to one another in a shielding layer substrate 741. In this example, the rods 743 are elongate to extend across a large portion of the substrate 741 width, such as 90%, 95%, 99% or more. In this example, the rods 743 are arranged in seven rows and a single column, with an equal space between each row. In other embodiments, any other number of rows, or other arrangement of rods, may be used, such as to meet one or more requirements of a patient's treatment plan. For example, a shielding layer substrate having an area of 2.5 cm×2.5 cm might achieve similar shielding of radiation though use of 10 rods having diameters of 2 mm (with about 0.5 mm space between the rods) and 100 rods having diameters of 0.02 mm (with about 0.005 mm space between the rods). However, one or more of various attributes of the shielding layer may differ between the two arrangements (and quantities) of rods. For example, the shielding layer with 100 rods may provide greater malleability, but increase heating and imaging artifacts, compared to the shielding layer with 10 rods. As shown in the side cross-section view 742, the rods are centered within the shielding layer substrate 741. However, in other embodiments, the rods may be offset within the shielding layer substrate 741, such as to provide more (or less) spacing between the radiation sources (e.g., carriers loaded with radioactive seeds) and the shielding materials. In this example, the rods with various cross-sections profiles are shown in end view 744. In some embodiments, cross-sectional profile of the rods may be selected based on radiation shielding, imaging artifact potential, heating potential, malleability, availability, cost, and/or other factors associated with the various rod shapes. For example, cross-sectional end view 744D illustrates rods having a generally hemispherical shape, which may provide increased malleability and reduced heating when compared to certain other cross-sectional profiles, such as circular or rectangular.

Figure 7F:
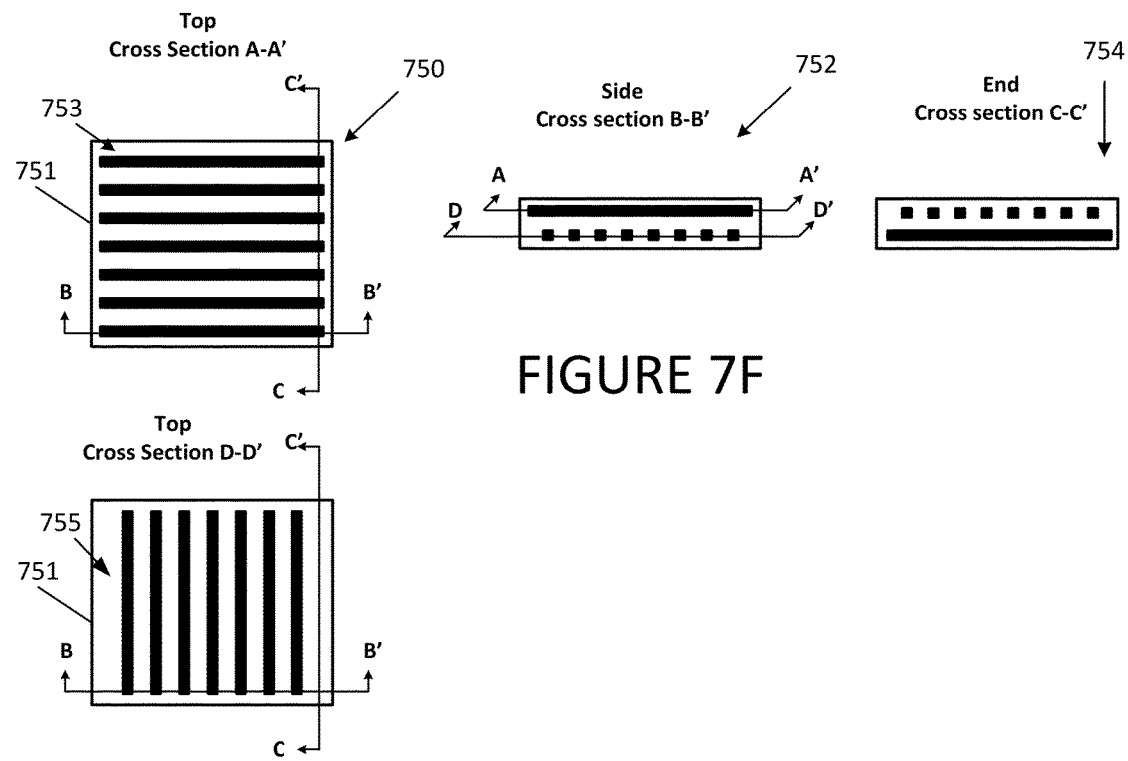

In the example isolation sheet of FIG. 7F, two sets of bars 753 and 755 are arranged in layers of the shielding layer substrate 751, such as to provide additional radiation blocking and/or absorption. In this example, multiple bars 753 are spaced uniformly in rows in an upper portion of the substrate 751 with a second set of multiple bars 755 spaced uniformly in columns in a lower portion of the substrate 751, as shown in side cross sectional view 752. As with other example embodiments discussed herein, the quantity, size, and spacing of the bars 753, 755 may vary from the configuration illustrated, such as to include a larger quantity and smaller size of bars (see example FIG. 7E, above). As shown in the side cross-section view 752, the bars 753 are spaced from the bars 755. In other embodiments, the bars may be spaced further or closer from one another. In this example, the bars have a substantially rectangular cross-sectional views 752 and 754. In other embodiments, bars may have varying cross-sectional profiles, such as triangular, pentagon hexagonal, etc.

Figure 7G:
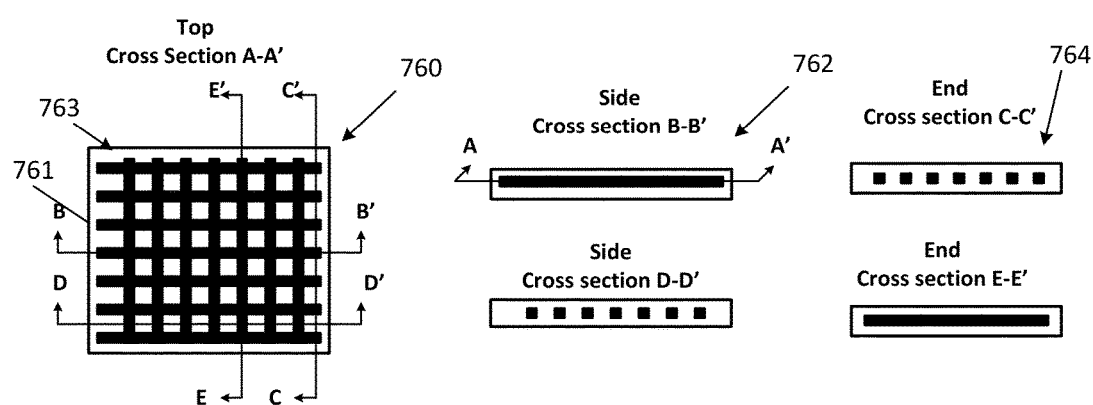

In the example isolation sheet of FIG. 7G, a mesh of shielding materials 763 embedded in a shielding layer substrate 761 is illustrated. The shielding materials 763 may be formed in the mesh pattern by a manufacturer (e.g., of the mesh pattern of shielding materials 763 or of the substrate pre-loaded with the shielding materials 763) or by a surgeon, for example, prior to implantation of the radioactive sources. In various embodiments, the multiple vertical and horizontal shielding materials may be in various shapes, such as bars, rods, wires, cylinders, etc. In the particular example of FIG. 7G, the shielding materials each have a substantially square cross-sectional shape, as illustrated in side view 762 and end view 764. In other embodiments, the vertical and horizontal shielding materials may have different shapes, sizes, cross-sectional profiles, etc. As with other example embodiments discussed herein, the quantity, size, and spacing of the shielding materials 763 may vary from the configuration illustrated, such as to include a larger quantity and smaller size of shielding materials. As shown in the cross-sectional views 762 and 764, the shielding materials 763 are centered within a height of the substrate 761. In other embodiments, the shielding materials may be closer to a top (or bottom surface).

Figure 7H:
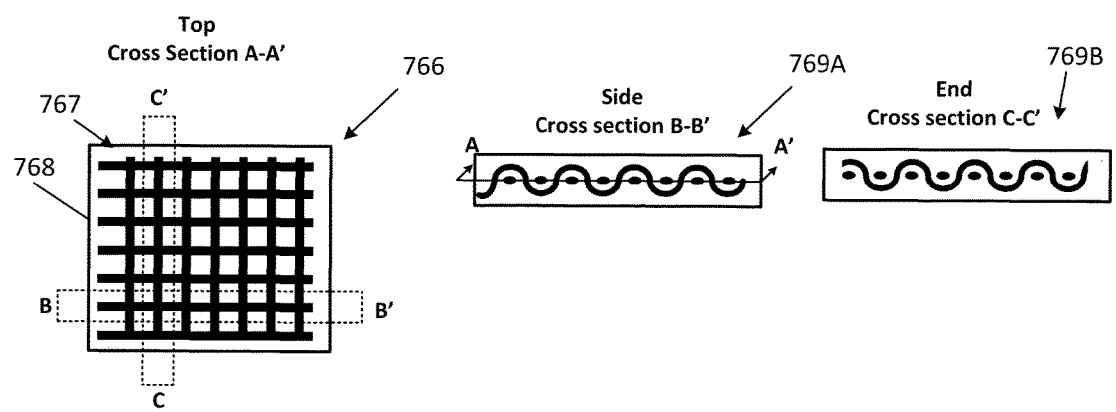

FIG. 7H illustrates an isolation sheet 766 including shielding materials 763 woven into a mesh pattern within a substrate layer 768. In other embodiments, such as mesh shielding material formed in this, or other, mesh patter may not be included in a substrate layer, such as because the intertwining of the substrate materials to form the mesh may provide sufficient adherence between the shielding materials to remove need for a separate substrate. In the embodiment of FIG. 7H, the shielding materials may comprise rods, wires, or other shielding materials, that are pre-formed by a manufacturer in the mesh pattern illustrated in side cross section 769A and end cross section 769B, or another mesh pattern.

Figure 7I:
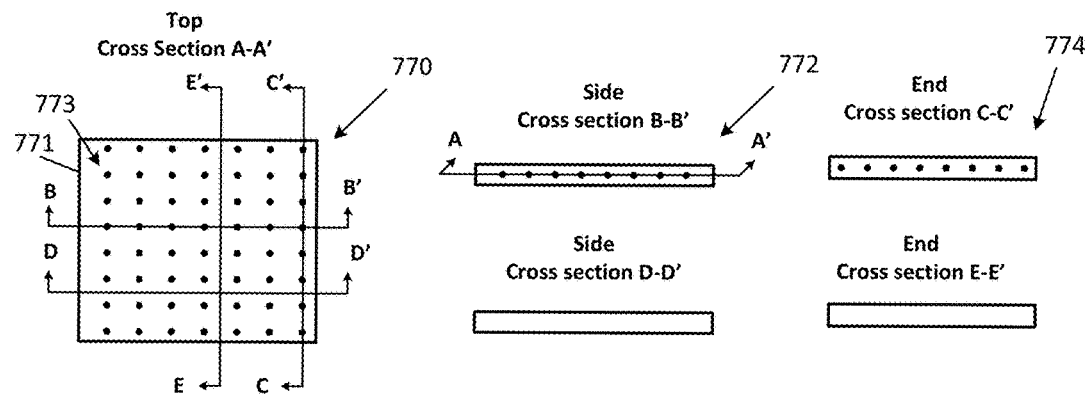
Figure 7J:
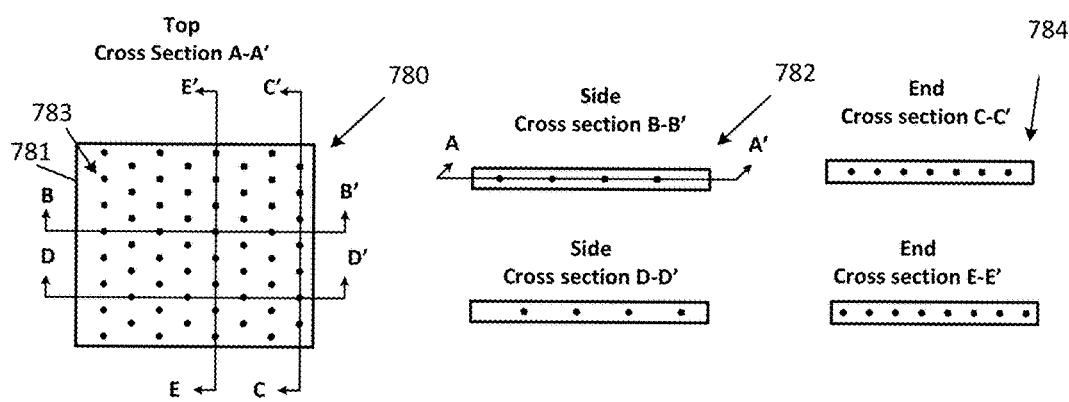
Figure 7K:
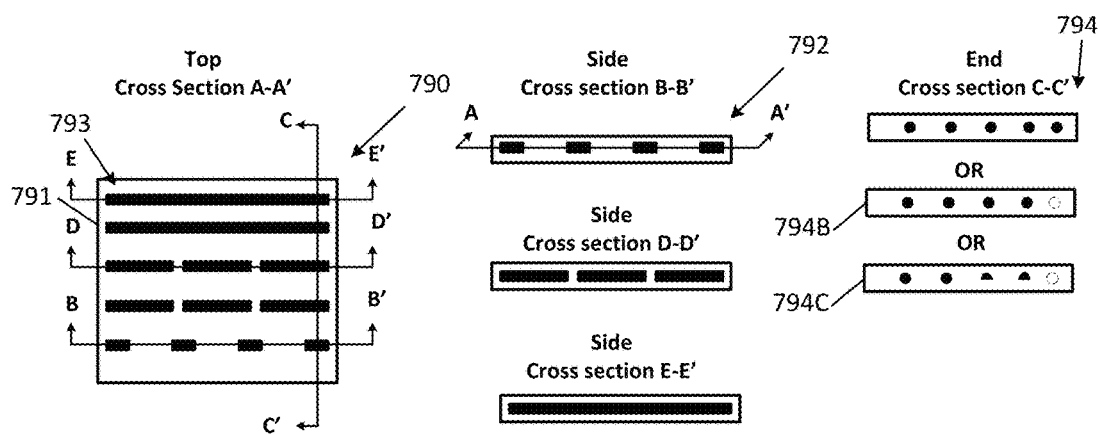

In the example isolation sheet of FIGS. 7I & 7J, multiple dots (or spheres) 773 and 783 are illustrated in different configurations within shielding layer substrates 771 and 781. In particular, dots 773 of FIG. 7I are positioned with the dots align in multiple rows and columns, as shown in the various views 770, 772, and 774. In FIG. 7J, however, the dots 783 are positioned in columns (and rows) such that dots in adjacent columns (and rows) are offset from one another, as shown in side cross-sectional views 782 and 784. Such an offset spacing may provide one or more of various advantages over uniformly spaced dots, such as greater radiation shielding with a comparable quantity of equivalent dots. As shown in the side cross-sectional views 772 and 782, the dots are centered within the shielding layer substrates 771 and 781, respectively. However, in other embodiments, the dots may be offset within the shielding layer substrates 771 and 781, such as to provide more (or less) spacing between the radiation sources (e.g., carriers loaded with radioactive seeds) and the dots. In other examples, other shielding materials, such as rods, cylinders, etc., may be positioned in an offset pattern similar to illustrated in FIG. 7J.

Figure 7L:
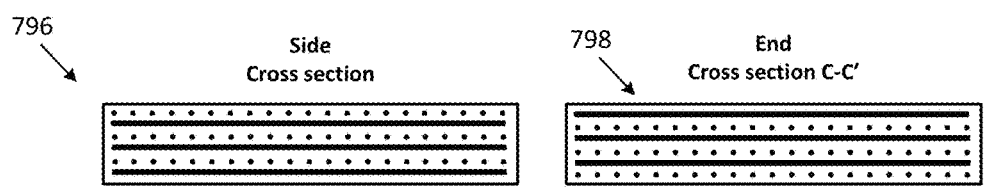

In the example isolation sheet of FIG. 7L, cross-sectional side view 796 and end view 798 illustrate multiple rows of rods. In this example, an upper portion of the isolation sheet includes a set of parallel rods across a width of a shielding layer substrate, followed by a set of parallel rods that are each perpendicular to the upper row of rods, and then additional rows and columns of rods. As with other example embodiments discussed herein, the quantity, size, spacing, quantity of layers, etc. of the rods (and/or other shielding materials used as an alternative, or addition, to rods) may vary from the configuration illustrated.

Figure 8:
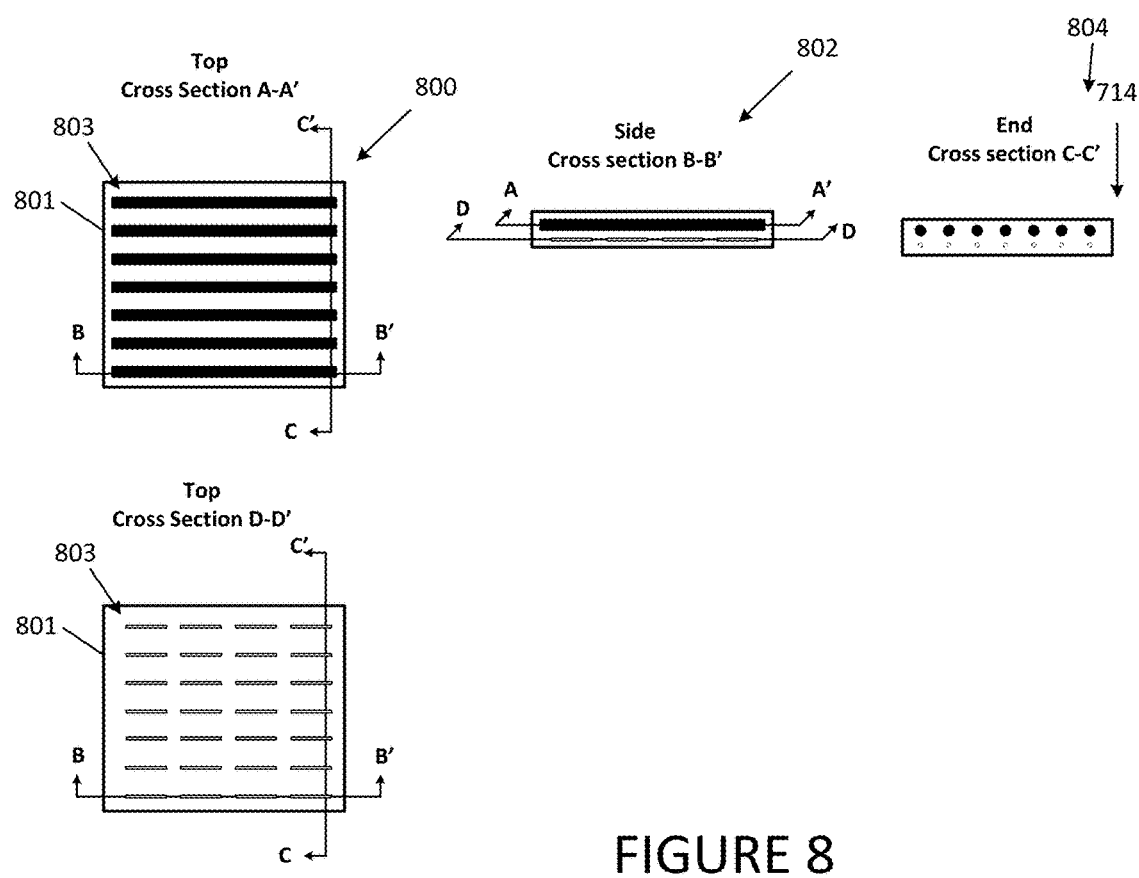
FIG. 8 illustrates an example isolation sheet adjacent radioactive seeds in a substrate.

FIG. 8 illustrates an example isolation sheet 800 adjacent radioactive seeds in a substrate 801. In this example, multiple parallel rods are positioned in an upper portion of the substrate 801, while multiple rows and columns of radioactive seeds 803 are positioned in a lower portion of the substrate 801. Thus, the composite isolation sheet 800 may replace the need for multiple radiation sources (e.g. hot carriers) and a separate isolation sheet, saving the treatment planning staff, surgeon, and possibly the patient, time and effort in implementation of the treatment plan. Additionally, this configuration may increase accuracy of a treatment plan by ensuring that the radiation sources are in a proper configuration with reference to one another, and also by ensuring that the desired shielding is properly aligned with the radiation sources.

Other Embodiments

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, the use of particular terminology when describing certain features or aspects of the invention should not be taken to imply that the terminology is being redefined herein to be restricted to including any specific characteristics of the features or aspects of the invention with which that terminology is associated. The scope of the invention should therefore be construed in accordance with the appended claims and any equivalents thereof.

What is claimed is:

1. A shielding apparatus comprising:
   a substrate; and
   a plurality of shielding materials positioned within the substrate at positions substantially matching positions of a corresponding plurality of radiation sources, at least some of the radiation sources arranged with gaps between the at least some of the radiations sources and adjacent of the plurality of radiation sources;
   wherein the apparatus is adapted for placement on the plurality of radiation sources so that each of the shielding materials provides substantial shielding of radiation emitted by a corresponding radiation source.

2. The shielding apparatus of claim 1, wherein gaps comprise collagen of the substrate between shielding materials.

3. The shielding apparatus of claim 1, wherein substantial shielding shields more than 80% of radiation.

4. The shielding apparatus of claim 1, wherein the shielding materials are formed in the shape of rods, cylinders, or spheres.

5. The shielding apparatus of claim 1, wherein a dosimetric plan indicates x*y radiation sources arranged in x rows and y columns, and the substrate is embedded with x*y shielding materials in x rows and y columns.

6. The shielding apparatus of claim 5, wherein the dosimetric plan indicates a gap distance between adjacent radiation sources in each of the x rows, and the shielding materials in each of the x rows are spaced apart by the gap distance.

7. The shielding apparatus of claim 6, wherein the dosimetric plan indicates a second gap distance between adjacent radiation sources in each of the y columns, and the shielding materials in each of the y columns are spaced apart by the second gap distance.

8. The shielding apparatus of claim 1, wherein a dosimetric plan indicates an irregular arrangement of the plurality of radiation sources, and the shielding materials are positioned in the same irregular arrangement in the substrate.

9. The shielding apparatus of claim 1, wherein the shielding apparatus is sufficiently malleable to be formed into a substantially hemispherical shape within a corresponding substantially hemispherical cavity.

10. The shielding apparatus of claim 1, wherein the substrate is adhered to a bio-compatible material.

11. The shielding apparatus of claim 1, wherein substantial shielding shields more than 50% of radiation.

12. An apparatus comprising:
    a substrate including:
       a radiation layer comprising a plurality of radiation sources positioned within the substrate, at least some of the radiation sources arranged with gaps between the at least some of the radiations sources; and
       a shielding layer comprising a plurality of shielding materials positioned within the substrate at positions substantially matching positions of radiation sources;
    wherein the shielding layer is adapted to provide substantial shielding of radiation emitted by radiation layer.

13. The apparatus of claim 12, wherein the shielding materials are formed in the shape of rods, cylinders, or spheres.

14. The apparatus of claim 12, wherein the plurality of radiation sources are arranged into x rows and y columns within the radiation layer.

15. The apparatus of claim 12, wherein the plurality of shielding materials are arranged into x rows and y columns within the shielding layer.

16. The apparatus of claim 12, wherein substantial shielding shields more than 50% of radiation incident on the shielding layer.

17. The apparatus of claim 16, wherein the shielding layer reflects radiation towards the radiation layer.

18. The apparatus of claim 12, wherein a first shielding material of the plurality of shielding materials is positioned within the shielding layer to provided substantial shielding to a plurality of radiation sources in the radiation layer.

19. The apparatus of claim 18, wherein the first shielding material comprises an elongated rod.

20. A manufacturing method comprising:
    positioning a plurality of shielding materials within a shielding substrate at positions substantially matching a corresponding plurality of radiation sources within a radiation substrate, at least some of the radiation sources arranged with gaps between the at least some of the radiation sources;
    wherein the shielding materials are adapted to provide substantial shielding of radiation emitted by corresponding radiation sources.

21. The manufacturing method of claim 20, wherein the shielding substrate and radiation substrate are layers of a biocompatible material.

22. The manufacturing method of claim 21, wherein the biocompatible material is collagen.

* * * * *

UNITED STATES PATENT AND TRADEMARK OFFICE
CERTIFICATE OF CORRECTION

PATENT NO. : 10,085,699 B2
APPLICATION NO. : 15/377014
DATED : October 2, 2018
INVENTOR(S) : David Brachman et al.

Page 1 of 1

It is certified that error appears in the above-identified patent and that said Letters Patent is hereby corrected as shown below:

In the Specification

In Column 1, Line 48, change "FIG." to --FIGS.--

In Column 4, Line 39, change "material(s)s," to --material(s),--

In Column 14, Line 54, change "FIG." to --FIGS.--

In Column 15, Lines 8-9, change "lypholization" to --lyophilization--

In Column 20, Line 7, change "FIG." to --FIGS.--

In the Claims

In Column 23, Line 19, Claim 1, change "radiations" to --radiation--

In Column 24, Line 34 (Approx.), Claim 18, change "provided" to --provide--

Signed and Sealed this
Twenty-sixth Day of February, 2019

Andrei Iancu
*Director of the United States Patent and Trademark Office*